(12) United States Patent
Davies et al.

(10) Patent No.: US 6,911,442 B1
(45) Date of Patent: Jun. 28, 2005

(54) QUINOLINE DERIVATIVES AS ANTIBACTERIALS

(75) Inventors: David Thomas Davies, Ware (GB); Roger Edward Markwell, Great Dunmow (GB); Neil David Pearson, Knebworth (GB); Andrew Kenneth Takle, Great Dunmow (GB)

(73) Assignee: SmithKline Beecham p.l.c., Brentford (GB)

( * ) Notice: Subject to any disclaimer, the term of this patent is extended or adjusted under 35 U.S.C. 154(b) by 63 days.

(21) Appl. No.: 10/018,900
(22) PCT Filed: Jun. 13, 2000
(86) PCT No.: PCT/EP00/05466
§ 371 (c)(1), (2), (4) Date: Aug. 1, 2002
(87) PCT Pub. No.: WO00/78748
PCT Pub. Date: Dec. 28, 2000

(30) Foreign Application Priority Data

Jun. 21, 1999 (GB) ............................................. 9914486

(51) Int. Cl.$^7$ .................... C07D 515/04; C07D 403/06; A61K 31/5365; A61K 31/506; A61P 31/04
(52) U.S. Cl. ............... 514/230.5; 514/248; 514/252.17; 514/253.04; 514/253.06; 544/105; 544/235; 544/283; 544/362; 544/363
(58) Field of Search ............................. 514/229.2, 248, 514/252.17, 253.04, 253.06, 230.5; 544/105, 235, 283, 362, 363

(56) References Cited

U.S. PATENT DOCUMENTS

| | | | |
|---|---|---|---|
| 3,230,223 A | 1/1966 | Baget et al. | 544/263 |
| 5,721,237 A | 2/1998 | Myers et al. | 514/266.2 |
| 6,403,610 B1 | 6/2002 | Malleron et al. | 514/314 |
| 6,602,882 B1 * | 8/2003 | Davies et al. | 514/300 |

FOREIGN PATENT DOCUMENTS

| | | |
|---|---|---|
| EP | 0238868 | 2/1987 |
| EP | 0304493 | 3/1988 |
| EP | 0296560 | 12/1988 |
| EP | 0374095 | 12/1989 |
| EP | 0541486 | 10/1992 |
| EP | 0579263 | 1/1994 |
| EP | 0742207 | 11/1996 |
| EP | 0823429 | 2/1998 |
| GB | 1496371 | 12/1997 |
| JP | 7179407 | 7/1995 |
| JP | 2169569 | 6/1999 |
| WO | WO9217475 | 10/1992 |
| WO | WO9509853 | 9/1994 |
| WO | WO9615128 | 5/1996 |
| WO | WO9639145 | 12/1996 |
| WO | WO9703069 | 1/1997 |
| WO | WO9717973 | 5/1997 |
| WO | WO9728167 | 8/1997 |
| WO | WO9802438 | 1/1998 |
| WO | WO9905096 | 4/1999 |
| WO | WO9937635 | 7/1999 |
| WO | WO0021948 | 4/2000 |
| WO | WO0021952 | 4/2000 |
| WO | WO0043383 | 7/2000 |

OTHER PUBLICATIONS

Kayirere M–G, et al., "Synthesis and antibacterial activity of new 4–alkoxy, 4–aminoalkyl and 4–alkylthioquinoline derivatives" European Journal of Medicinal Chemistry. Chimica Therapeutica., vol. 33, No. 1, 1998 pp. 55–63 XP004173056 Editions Scientifique Elsevier, Paris., FR ISSN: 0223–5234 p. 55–p. 56.

* cited by examiner

*Primary Examiner*—Thomas McKenzie
(74) *Attorney, Agent, or Firm*—Grace C. Hsu; Mary McCarthy; Charles M. Kinzig

(57) ABSTRACT

The present invention relates to a compound of formula (I) or a pharmaceutically acceptable salt and/or N-oxide thereof:

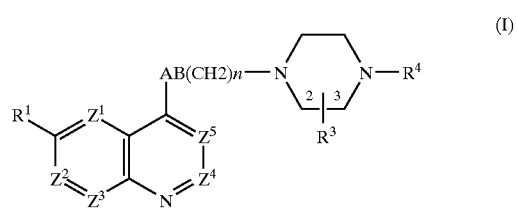

corresponding novel medicaments, pharmaceutical compositions and/or methods of

11 Claims, No Drawings

QUINOLINE DERIVATIVES AS ANTIBACTERIALS

This is a 371 of International Application PCT/EP00/05466, filed 13 Jun. 2000, which claims benefit from the following Provisional Application; 9914486.7 GB, filed 21 Jun. 1999.

This invention relates to novel medicaments, being novel antibacterial compounds and compositions.

EP0579263, EP0742207, JP2169569 and EP0296560, generically disclose piperazine compounds as acetylcholinesterase inhibitors and sigma receptor antagonists WO9217475, WO9802438, WO9703069 and WO9639145 disclose certain bicyclic heteroaromatic compounds having cholinesterase inhibitor, protein tyrosine kinase inhibitor, cell proliferation inhibitor and human epidermal growth factor receptor type 2 inhibitor activity.

This invention provides a compound of formula (I) or a pharmaceutically acceptable salt and/or N-oxide thereof:

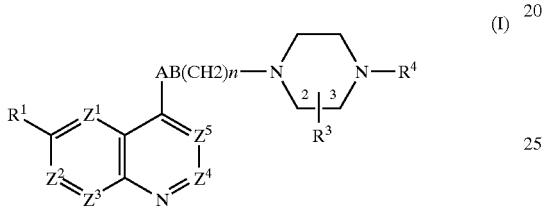

wherein:
one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;

$R^1$ is selected from hydroxy; $(C_{1-6})$ alkoxy optionally substituted by $(C_{1-6})$alkoxy, amino, piperidyl, guanidino or amidino optionally N-substituted by one or two $(C_{1-6})$alkyl, acyl or $(C_{1-6})$alkylsulphonyl groups, $NH_2CO$, hydroxy, thiol, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted $(C_{1-6})$alkyl; halogen; $(C_{1-6})$alkyl; $(C_{1-6})$alkylthio; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups, or when one of $Z^1$, $Z^2$, $Z^3$, $Z^4$ and $Z^5$ is N, $R^1$ may instead be hydrogen;

$R^{1a}$ is selected from H and the groups listed above for $R^1$;
$R^3$ is in the 2- or 3-position and is:
carboxy; $(C_{1-6})$alkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$atkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetnizol-5-ylaminocarbonyl; 1,2,4-triazol-5-yl optionally substituted by $R^{10}$; or 5-oxo-1,2,4-oxadiazol-3-yl; or $R^3$ is in the 2- or 3-position and is $(C_{1-4})$alkyl or ethenyl optionally substituted with any of the groups listed above for $R^3$ and/or 0 to 3 groups $R^{12}$ independently selected from:

thiol; halogen; $(C_{1-6})$alkylthio; trifluoromethyl; azido; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

provided that when $R^3$ is disubstituted with hydroxy or amino and carboxy containing substituents these may optionally together form a cyclic ester or amide linkage, respectively;

wherein $R^{10}$ is selected from $(C_{1-4})$alkyl; $(C_{2-4})$alkenyl; aryl; a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; cyano; or tetrazolyl;

$R^4$ is a group $—CH_2—R^5$ in which $R^5$ is selected from: $(C_{3-12})$alkyl; hydroxy$(C_{3-12})$alkyl; $(C_{1-12})$alkoxy$(C_{3-12})$alkyl; $(C_{1-12})$alkanoyloxy$(C_{3-12})$alkyl; $(C_{3-6})$cycloalkyl$(C_{3-12})$alkyl; hydroxy-, $(C_{1-12})$alkoxy- or (C1-12)alkanoyloxy-$(C_{3-6})$cycloalkyl$(C_{3-12})$alkyl; cyano$(C_{3-12})$alkyl; $(C_{2-12})$alkenyl; $(C_{2-12})$alkynyl; tetrahydrofuryl; mono- or di-$(C_{1-12})$alkylamino$(C_{3-12})$alkyl; acylamino$(C_{3-12})$alkyl; $(C_{1-12})$alkyl- or acyl-aminocarbonyl$(C_{3-12})$alkyl; mono- or di-$(C_{1-12})$alkylamino(hydroxy)$(C_{3-12})$alkyl; optionally substituted phenyl$(C_{1-2})$alkyl, phenoxy$(C_{1-2})$alkyl or phenyl(hydroxy)$(C_{1-2})$alkyl; optionally substituted diphenyl $(C_{1-2})$alkyl; optionally substituted phenyl $(C_{2-3})$alkenyl; optionally substituted benzoyl or benzoyl$(C_{1-3})$alkyl; optionally substituted heteroaryl or heteroaryl$(C_{1-2})$alkyl;and optionally substituted heteroaroyl or heteroaroylmethyl;

n is 0 or 2;

AB is $NR^{11}CO$, CO—$CR^8R^9$ or $CR^6R^7$—$CR^8R^9$ or when n is 1 or 2, AB may instead be O—$CR^8R^9$ or $NR^{11}$—$CR^8R^9$, or when n is 2 AB may instead be $CR^6R^7$—$NR^{11}$ or $CR^6R^7$—O, provided that when n is 0, B is not CH(OH), and wherein:
each of $R^6$ and $R^7$, $R^8$ and $R^9$ is independently selected from: H; thiol; $(C_{1-6})$alkylthio; halo; trifluoromethyl;

azido; (Cl6)alkyl; ($C_{2-6}$)alkenyl; ($C_{1-6}$)alkoxycarbonyl; ($C_{1-6}$)allkylcarbonyl; ($C_{2-6}$)alkenyloxycarbonyl; ($C_{2-6}$)alkenylcarbonyl; hydroxy, amino or aminocarbonyl optionally substituted as for corresponding substituents in $R^3$; ($C_{1-6}$)alkylsulphonyl; ($C_{2-6}$)alkenyisulphonyl; or ($C_{1-6}$)aminosulphonyl wherein the amino group is optionally substituted by ($C_{1-6}$)alkyl or ($C_{1-6}$)alkenyl;

or $R^6$ and $R^8$ together represent a bond and $R^7$ and $R^9$ are as above defined; and each $R^{11}$ is independently H, trifluoromethyl, ($C_{1-6}$)alkyl, ($C_{2-6}$)alkenyl, ($C_{1-6}$) alkoxycarbonyl, ($C_{1-6}$)alkylcarbonyl, aminocarbonyl wherein the amino group is optionally substituted by ($C_{1-6}$)alkoxycarbonyl, ($C_{1-6}$)alkylcarbonyl, ($C_{2-6}$) alkenyloxycarbonyl, ($C_{2-6}$)alkenylcarbonyl, ($C_{1-6}$) alkyl or ($C_{2-6}$)alkenyl and optionally further substituted by ($C_{1-6}$)alkyl or ($C_{2-6}$)alkenyl; or where one of $R^3$ and $R^6$, $R^7$, $R^8$ or $R^9$ contains a carboxy group and the other contains a hydroxy or amino group they may together form a cyclic ester or amide linkage wherein:

'heterocyclic' is an aromatic and non-aromatic. sinele or fused, rine containing up to four hetero-stoms in each rine selected from oxvyen, nitroeen and sulphur, and having from 4 to 7 rinn atoms, which rings may be unsubstituted or substituted by up to three groups selected from amino, halogen, ($C_{1-6}$) alkyl, ($C_{1-6}$)alkoxy, halo($C_{1-6}$)alkyl, hydroxy, carboxy, carboxy salts, ($C_{1-6}$)alkoxvcarbonyl, ($C_{1-6}$) alkoxycarbonyl($C_{1-6}$)alkyl, aryl, and oxo groups, and wherein any amino group forming part of a single or fused non-aromatic heterocyclic ring as defined above is optionally substituted by ($C_{1-6}$)alkyl optionally substituted by hydroxy, ($C_{1-6}$)alkoxy, thiol, ($C_{1-6}$)alkylthio, halo or trifluoromethyl, acyl or ($C_{1-6}$) alkylsulphonyl groups;

'aryl' is phenyl or naphthyl, optionally substituted with up to five groups selected from halogen, mercapto, ($C_{1-6}$)alkyl, phenyl, ($C_{1-6}$)alkoxy, hydroxy($C_{1-6}$) alkyl, mercapto ($C_{1-6}$)alkyl, halo($C_{1-6}$)alkyl, hydroxy, amino, nitro, cyano, carboxy, ($C_{1-6}$) alkylcarbonyioxy, ($C_{1-6}$)alkoxycarbonyl, formyl and ($C_{1-6}$)alkylcarbonyl groups;

'acyl' is ($C_{1-6}$)alkoxycarbonyl, formyl or ($C_{1-6}$) alkyicarbonyl.

The invention also provides the use of a compound of formula (I) or a pharmaceutically acceptable salt and/or Noxide thereof in the manufacture of a medicament for use in the treatment of bacterial infections in mammals.

The invention also provides a pharmaceutical composition for use in the treatment of bacterial infections in mammals comprising a compound of formula (I), or a pharmaceutically acceptable salt and/or N-oxide thereof, and a pharmaceutically acceptable carrier.

The invention further provides a method of treatment of bacterial infections in mammals, particularly in man, which method comprises the administration to a mammal in need of such treatment of an effective amount of a compound of formula (I), or a pharmaceutically acceptable salt and/or N-oxide thereof.

In one aspect, when n=1 B is not CH(OH).

In a further aspect $R^5$ is not optionally substituted benzoyl ($C_{2-3}$)alkyl or optionally substituted heteroaryl.

Preferably one of $Z^1$, $Z^2$, $Z^3$, $Z^4$ and $Z^5$ is N and one of $Z^3$ and $Z^5$ if not N is $CR^{1a}$ and the remainder are CH, or one of $Z^1$, $Z^2$, $Z^3$, $Z^4$ and $Z^5$ is $CR^{1a}$ and the remainder are CH.

More preferably $Z^5$ is CH or N, $Z^3$ is CH or CF and $Z^1$, $Z^2$ and $Z^4$ are each CH, or $Z^1$ is N, $Z^3$ is CH or CF and $Z^2$, $Z^4$ and $Z^5$ are each CH. Most preferably $Z^1$-$Z^5$ are each CH.

When $R^1$ or $R^{1a}$ is substituted alkoxy it is preferably $C_{2-6}$ alkoxy substituted by optionally N-substituted amino, guanidino or amidino, or $C_{1-6}$alkoxy substituted by piperidyl. Suitable examples of RI alkoxy include methoxy, n-propyloxy, i-butyloxy, aminoethyloxy, aminopropyloxy, aminopentyloxy, guanidinopropyloxy, piperidin-4-ylmethyloxy, phthalimido pentyloxy or 2-aminocarbonylprop-2-oxy. Preferably $R^1$ is methoxy, amino($C_{3-5}$)alkyloxy, guanidino($C_{3-5}$)alkyloxy, piperidyl ($C_{3-5}$)alkyloxy, nitro or fluoro.

Preferably $R^{1a}$ is hydrogen or when $Z^3$ is $CR^{1a}$ it may be C-F.

In one aspect, $R^3$ is preferably hydrogen, ($C_{1-4}$) alkyl, ethenyl, or 1-hydroxy-($C_{1-4}$) alkyl optionally substituted as defined in formula (I), more preferably hydroxymethyl, 1,2-dihydroxy($C_{2-4}$)alkyl wherein the 2-hydroxy group is optionally substituted as defined in formula (I). Preferred examples of $R^3$ include hydroxymethyl, 1-hydroxyethyl or 1,2-dihydroxyethyl wherein the 2-hydroxy group is optionally substituted with alkylcarbonyl or aminocarbonyl where the amnino group is optionally substituted as defined in formula (I). Other suitable examples of $R^3$ include 2-hydroxyethyl, 2- or 3-hydroxypropyl, ethyl or ethenyl.

In another aspect $R^3$ preferably contains carboxy, aminocarbonyl optionally substituted as defined in formula (I), cyano or 2-oxo-oxazolidinyl optionally substituted by $R^{10}$. Where $R^3$ is substituted alkyl is it preferably substituted methyl. Preferred examples of $R^3$ include $CO_2H$, $CH_2CO_2H$, $(CH_2)_2CO_2H$, $(CH_2)_2CN$, $CH(OH)CH_2CN$, $CH(OH)CH_2CO_2H$, $CH=CHCO_2H$ or 2-oxo-oxazolidinyl.

$R^3$ is preferably in the 3-position.

When $R^3$ and $R^6$, $R^7$, $R^8$ or $R^9$ together form a cyclic ester or amide linkage, it is preferred that the resulting ring is 5-7 membered. It is further preferred that the group A or B which does not form the ester or amide linkage is $CH_2$.

When A is CH(OH) the R-stereochemistry is preferred.

Preferably A is NH, $NCH_3$, $CH_2$, CHOH, $CH(NH_2)$, C(MeX)(OH) or CH(Me) or, only when n=2, O.

Preferably B is $CH_2$ or CO or, only when n=2, CHOH.

Preferably n is 0 or 1.

More preferably n=0.

Most preferably:

n is 0 and either A is CHOH and B is $CH_2$ or A is NH and B is CO.

Suitable groups $R^4$ include n-pentyl, n-hexyl, n-heptyl, n-octyl, n-nonyl, n-decyl, n-dodecyl, 5-methylhexyl, 6-methylbeptyl, methoxybutyl, phenylethyl, phenylpropyl or 3-phenyl-prop-2-en-yl optionally substituted on the phenyl ring, 3-benzoylpropyl, 4-benzoylbutyl, 3-pyridylmethyl, 3-(4fluorobenzoyl)propyl, cyclohexylmethyl, cyclobutylmethyl, t-butoxycarbonylaminomethyl, phenoxyethyl and 3-(1,3-dihydro-2-oxo-benzimidazolyl)propyl.

Preferably $R^4$ is ($C_{5-10}$)alkyl, unsubstituted phenyl($C_{2-3}$) alkyl or unsubstituted phenyl($C_{3-4}$)alkenyl, more preferably hexyl, heptyl, 5-methylhexyl, 6-methyl heptyl, 3-phenyl-prop-2-en-yl or 3-phenylpropyl, most preferably heptyl.

Most preferably $R^5$ is unbranched at the a and, where appropriate, P positions.

Halo or halogen includes fluoro, chloro, bromo and iodo.

The term 'heterocyclic' as used herein includes aromatic and non-aromatic, single and fused, rings suitably containing up to four hetero-atoms in each ring selected from oxygen, nitrogen and sulphur, which rings may be unsubstituted or substituted by, for example, up to three groups selected from optionally substituted amino, halogen, ($C_{1-6}$) alkyl, ($C_{1-6}$)alkoxy, halo($C_{1-6}$)alkyl, hydroxy, carboxy, carboxy salts, carboxy esters such as ($C_{1-6}$)alkoxycarbonyl, ($C_{1-6}$)alkoxycarbonyl($C_{1-6}$)alkyl, aryl, and oxo groups. Each heterocyclic ring suitably has from 4 to 7, preferably 5 or 6, ring atoms. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include ($C_{1-6}$)alkyl optionally substituted by hydroxy, ($C_{1-6}$)alkoxy, thiol, ($C_{1-6}$)alkylthio, halo or trifluoromethyl, and amino-protecting groups such as acyl or ($C_{1-6}$) alkylsulphonyl groups.

The term 'heteroaryl' includes the aromatic heterocyclic groups referred to above. Examples of heteroaryl groups include pyridyl, triazolyl, tetrazolyl, indolyl, thienyl, isoimidazolyl, thiazolyl, furanyl,quinolinyl, imidazolyl, 1,3-dihydro-2-oxo-benzimidazolyl and benzothienyl.

When used herein the term 'aryl', includes phenyl and naphthyl, each optionally substituted with up to five, preferably up to three, groups selected from halogen, mercapto, ($C_{1-6}$)alkyl, phenyl, ($C_{1-6}$)alkoxy, hydroxy($C_{16}$)alkyl, mercapto ($C_{1-6}$)alkyl, halo($C_{1-6}$)alkyl, hydroxy, optionally substituted amino, nitro, cyano, carboxy, ($C_{1-6}$) alkylcarbonyloxy, ($C_{1-6}$)alkoxycarbonyl, formiyl, or ($C_{1-6}$) alkylcarbonyl groups.

The term 'acyl' includes ($C_{2-6}$)alkoxycarbonyl, fornyl or ($C_{2-6}$) alkylcarbonyl group. Aryl are preferably substituted with up to three groups.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or salt thereof.

Pharmaceutically acceptable derivatives of the above-mentioned compounds of formula (I) include the free base form or their acid addition or quaternary ammonium salts, for example their salts with mineral acids e.g. hydrochloric, hydrobromic or sulphuric acids, or organic acids, e.g. acetic, fumaric or tartaric acids. Compounds of formula (I) may also be prepared as the N-oxide.

Certain of the above-mentioned compounds of formula (I) may exist in the form of optical isomers, e.g. diastereoisomers and mixtures of isomers in all ratios, e.g. racemic mixtures. The invention includes all such forms, in particular the pure isomeric forms. For examples the invention includes compound in which an A–B group CH(OH)—CH$_2$ is in either isomeric configuration.

In a further aspect of the invention there is provided a process for preparing compounds of formula (I), or a pharmaceutically acceptable salt and/or N-oxide thereof, which process comprises:

(a) reacting a compound of formula (IV) with a compound of formula (V):

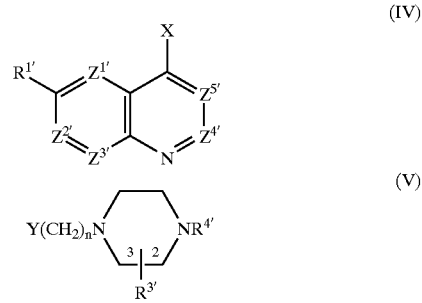

wherein $Z^1$, $Z^2$, $Z^3$, $Z^4$ and $Z^5$, m, n, $R^1$, $R^3$ and $R^4$ are as defined in formula (I), and X and Y may be the following combinations:

(i) X is M and Y is CH$_2$CO$_2$RX, CH$_2$CHO or CH$_2$COW
(ii) X is CO$_2$RY and Y is CH$_2$CO$_2$Rx
(iii) one of X and Y is CH=SPh$_2$ and the other is CHO
(iv) X is CH$_3$ and Y is CHO
(v) X is CH$_3$ and Y is CO$_2$Rx
(vi) X is CH$_2$CO$_2$RY and Y is CO$_2$RX
(vii) X is CH=PRZ$_3$ and Y is CHO
(viii) X is CHO and Y is CH=PRZ$_3$
(ix) X is halogen and Y is CH=CH$_2$
(x) one of X and Y is COW and the other is NHR$^{11'}$
(xi) one of X and Y is (CH$_2$)$_p$—W and the other is (CH$_2$)$_q$NHR$^{11}$ or (CH$_2$)$_q$OH
(xii) one of X and Y is CHO and the other is NHR$^{11'}$, or where n=0
(xiii) X is A–B-(CH$_2$)n-W or A–B-(CH2)nl-CHO and Y is H
(xiv) X is NCO and Y is H
(xv) X is CH$_3$ and Y is H
(xvi) X is COCH$_2$W and Y is H
(xvii) X is CH=CH$_2$ and Y is H
(xviii) X is oxirane and Y is H
in which W is a leaving group, Rx and RY are ($C_1$)alkyl and RZ is aryl or (Cl $_6$)alkyl;

or (b) reacting a compound of formula (IV) with a compound of formula (Vb):

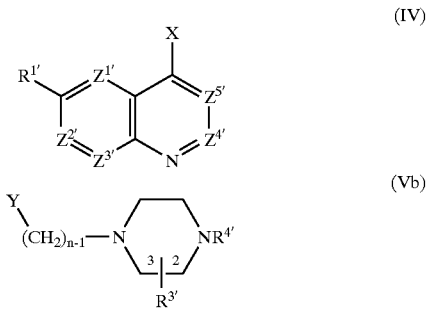

wherein $Z^1$, $Z^2$, $Z^3$, $Z^4$ and $Z^5$, m, n, RI, $R^3$ and $R^4$ are as defined in formula (I), X is CH$_2$NHR$^{11}$ and Y is CHO or COW;

in which $Z^{1'}$, $Z^{2'}$, $Z^{3'}$, $Z^{4'}$, $Z^{5}$, $R^{11'}$, $R^{1'}$, $R^{3'}$ and $R^{4'}$ are $Z^1$, $Z^2$, $Z^3$, $Z^4$, $Z^5$, $R^{11}$, $R^1$, $R^3$ and $R^4$ or groups convertible thereto, and thereafter optionally or as necessary converting $Z^{1'}, Z^{2'}, Z^{3'}, Z^{4'}, Z^{5'}, R^{11'}, R^{1'}, R^{3'}$ and $R^{4'}$ to $Z^1, Z^2, Z^3 Z^4, Z^5, R^{11}, R^1, R^3$ and $R^4$, converting A–B to other A–B, interconverting $Z^1, Z^2, Z^3, Z^4, Z^5, R^{11}, R^1, R^3$ and/or $R^4$ and forming a pharmaceutically acceptable salt and/or N-oxide thereof.

Process variants (a)(i) and (a)(ii) initially produce compounds of formula (I) where A–B is $COCH_2$or, in the case of Y=CHO, $CHOHCH_2$.

Process variant (axiii) initially produces compounds of formula (I) wherein A–B is $CH_2CHOH$ or $CHOHCH_2$.

Process variant (a)(iv) initially produces compounds of formula (I) wherein A–B is $CH_2CHOH$.

Process variants (a)(v) and (a)(vi), initially produce compounds of formula (I) wherein A–B is $CH_2CO$.

Process variants (a)(vii), (a)(viii) and (a)(ix) initially produce compounds where A–B is CH=CH.

Process variant (a)(x) initially produces compounds of formula (I) wherein A–B is $CONHR^{11}$ or $NHR^{11}CO$.

Process variant (a)(xi) initially produces compounds of formula (I) wherein one of A and B is $CH_2$ and the other is $NHR^{11}$ or O.

Process variant (a)(xii), initially produce compounds of formula (I) wherein A–B is $CH_2NHR^{11}$ or $NHR^{11}CH_2$.

Process variant (a)(xiii) initially produces compounds of formula (I) having an A-B-$(CH_2)_n$linker.

Process variant (a)(xiv) initially produces compounds of formula (I) where n is 0 and A–B is NHCO.

Process variant (a)(xv) initially produces compounds of formula (I) where n is 0 and A–B is $CH_2$—$CH_2$.

Process variant (a)(xvii) initially produce compounds of formula (I) where n is 0 and A–B is $CH_2CH_2$.

Process variant (a)(xvi) initially produces compounds of formula (I) where n is 0 and A–B is $COCH_2$.

Process variant (a)(xviii) initially produces compounds of formula (I) where n is 0 and A–B is $CHOHCH_2$.

Process variant (b) initially produces compounds of formula (I) wherein A is $CH_2$ and B is $NHR^{11}$.

In process variant (a)(i) M is preferably an alkali metal, more preferably Li. The reaction with an ester is conducted in an aprotic solvent preferably THF, ether or benzene at −78 to 25° C. An analogous route is described in G. Grethe et al (1972) Helv. Chimica.Acta., 55, 1044. Where the compound of formula (V) is an acid chloride, M is zinc or tin.. The reaction with an aldehyde gives the alcohol (A=CHOH).

In process variant (a)(ii) the process is two step: firstly a condensation using a base, preferably sodium hydride or alkoxide, sodamide, alkyl lithium or lithium dialkylamide, preferably in an aprotic solvent e.g. ether, THF or benzene; secondly, hydrolysis using an inorganic acid, preferably HCl in aqueous organic solvent at 0–100° C. Analogous routes are described in DE330945, EP31753, EP53964 and H. Sargent, J. Am. Chem. Soc. 68, 2688–2692 (1946).

In process variant (a)(iii) if a base is used it is preferably NaH, KH, an alkyl lithium e.g. BuLi, a metal alkoxide e.g. NaOEt, sodamide or lithium dialkylamide e.g.di-isopropylamide. An analogous method is described in U.S. Pat. No. 3,989,691 and in Taylor et al. (1972) JACS 94,6218)

In process variant (a)(iv) the reaction is carried out in the presence of a base, preferably organometallic or metal hydride e.g. NaH, lithium diisopropylamide or NaOEt, preferably in an aprotic solvent, preferably THF, ether or benzene at −78 to 25° C. (analogous process in Gutswiller et al. (1978) JACS 100, 576).

In process variant (a)(v) the reaction is carried out in the presence of a base, preferably organometallic or metal hydride e.g. NaH, lithium diisopropylamide or NaOEt, preferably in an aprotic solvent, preferably THF, ether or benzene at −78 to 25° C. An analogous method is described in U.S. Pat. No. 3,772,302.

In process variant (a)(vi) a similar Claisen methodology to that described for (a)(ii) is used, analogous to that described in Soszko et. al., Pr.Kom.Mat. Przyr.Poznan.Tow.Przyj.Nauk., (1962), 10, 15.

In process variants (a)(vii) and (viii) if a base is used it is preferably NaH, KH, an alkyl lithium e.g. BuLi, a metal alkoxide e.g. NaOEt, sodamide or lithium dialkylamide e.g. di-isopropylamide. An analogous method is described in U.S. Pat. No. 3989691 and M.Gates et. al. (1970) J. Amer.Chem.Soc., 92, 205, as well as Taylor et al. (1972) JACS 94, 6218.

In process variant (a)(ix) the reaction is carried out using palladium catalysis. The palladium catalyst is preferably palladium acetate in the presence of trialkyl or triaryl phosphine and a trialkylamine e.g. triphenyl phosphine and tributylamine. An analogous method is described in S. Adam et al. (1994) Tetrahedron, 50, 3327.

In process variant (a)(x), or (b) where Y is COW,the reaction is a standard amide formation reaction:
1. Activation of a carboxylic acid (e.g., to an acid chloride, mixed anhydride, active ester, O-acyl-isourea or other species), and treatment with an amine (Ogliaruso, M. A.; Wolfe, J. F. in *The Chemistry of Functional Groups* (*Ed Patai, S.*) *Suppl. B: The Chemistry of Acid Derivatives, Pt. I* (John Wiley and Sons, 1979), pp 442–8; Beckwith, A. L. J. in *The Chemistry of Functional Groups* (*Ed. Patai, S.*) *Suppi. B: The Chemistry of Amides* (*Ed Zabricy, J.*) (John Wiley and Sons, 1970), p 73 ff. The acid and amide are preferably reacted in the presence of an activating agent such as 1-(dimethylaminopropyl)-3-ethylcarbodiimide hydrochloride (EDC) and 1hydroxybenzotriazole (HOBT),
2. Aminolysis of esters (Suzuki, K.; Nagasawa, T. in *Encyclopedia of Reagents for Organic Synthesis* (*Ed. Paquette, L. A*) (John Wiley and Sons, 1995), p 5188 and refs. cited therein.)
3. The specific methods of:
a. in situ conversion of an acid into the amine component by a modified Curtius reaction procedure (Shioiri, T.; Murata, M.; Hamada, Y., *Chem. Pharm. Bull.* 1987, 35, 2698)
b. in situ conversion of the acid component into the acid chloride under neutral conditions (Villeneuve, G. B.; Chan, T. H., *Tet. Lett.* 1997, 38, 6489).

In process variant (b) a final reduction step provides the required amine.

In process variant (a)(xi) where one of X and Y contains $NHR^{11}$ the leaving group V is halogen and the reaction is a standard amine formation reaction such as direct alkylation described in (Malpass, J. R., in *Comprehensive Organic Chemistry*, Vol. 2 (Ed. Sutherland, I. O.), p 4 ff.) or aromatic nucleophilic displacement reactions (see references cited in *Comprehensive Organic Chemistry*, Vol. 6, p 946–947 (reaction index); Smith, D. M. in *Comprehensive Organic Chemistry*, Vol. 4 (Ed. Sammes, P. G.) p 20 ff.). This is analogous to the methods described in GB II 77.849.

In process variant (a)(xi) where one of X and Y contains OH, this is preferably converted to an OM group where M is an alkali metal by treatment of an alcohol with a 35 base. The base is preferably inorganic such as NaH, lithium diisopropylamide or sodium. Where X is OH and Y is $CH_2W$, W is a hydroxy group activated under Mitsunobu conditions (Fletcher et.al. J Chem Soc. (1995), 623).

In process variants (a)(xii) and (b) where Y is CHO the reaction is a standard reductive alkylation using, e.g., sodium triacetoxyborohydride (Gribble, G. W. in *Encyclopedia of Reagents for Organic Synthesis* (*Ed Paquefte, L. A.*) (John Wiley and Sons, 1995), p 4649).

Process variant (a)(xiii) is a simple amine formation reaction similar to variant (a)(xi) and (xii) above.

In process variant (a) (xvi) the reaction is carried out in the presence of an organic base such as triethylamine or an inorganic base such as potassium carbonate.

In process variant (a)(xiv) the reaction is carried out in the presence of base such as triethylamine.

In process variant (a)(xv) the reaction is carried out by condensing the compounds of formulae (IV) and (V) with formaldehyde under either basic or acidic conditions (A. Murti, Indian J. Chem. Vol2B, 1989, 934).

In process variant (a)(xvii) the reactants are combined in a polar organic solvent such as dichloromethane, methanol or DMF, optionally in the presence of an organic base such as tetramethylguanidine.

In process variant (a)(xviii) the coupling may be effected in acetonitrile at room temperature in the presence of one equivalent of lithium perchlorate as catalyst [general method of J. E. Chateauneuf et al. *J Org. Chem.* 56, 5939–5942]. In some cases an elevated temperature such as 40–70° C. may be beneficial. Alternatively, the piperazine may be treated with a base (such as one equivalent of butyl lithium) and the salt reacted with the epoxide in an inert solvent such as tetrahydrofuran, preferably at an elevated temperature such as 80° C. Use of a chiral epoxide will afford single diastereomers at C-2. Alternatively, mixtures of diastereomers may be separated by preparative HPLC or by conventional resolution through crystallisation of salts formed from chiral acids.

Reduction of A or B CO to CHOH can be readily accomplished using reducing agents well known to those skilled in the art, e.g. sodium borohydride in aqueous ethanol or lithium aluminiun hydride in ethereal solution.. This is analogous to methods described in EP 53964, U.S. Pat. No. 384,556 and J. Gutzwiller et al. (1978) J.Amer.Chem.Soc., 100, 576.

The carbonyl group A or B may be reduced to $CH_2$ by treatment with a reducing agent such as hydrazine in ethylene glycol at 130–60° C. in the presence of potassium hydroxide.

Reaction of a carbonyl group A or B with an organometallic reagent yields a group where $R^6$ or $R^8$ is OH and $R^7$ or $R^9$ is alkyl.

A hydroxy group in A or B may be oxidised to a carbonyl group by oxidants well known to those skilled in the art, for example, manganese dioxide, pyridinium chlorochromate or pyridinium dichromate.

An A–B group $COCH_2$ may be converted to COCH-halogen, by treating the ketone or a derivative with a halogenating agent, reduced to CHOHCHCl and then converted to the epoxide which may in turn be reduced to $CH_2CHOH$.

Methods for conversion of CH=CH by reduction to $CH_2CH_2$ are well known to those skilled in the art, for example using hydrogenation over palladium on carbon as catalyst. Methods for conversion of CH=CH to give the A–B group as $CHOHCH_2$ or $CH_2CHOH$ are well known to those skilled in the art for example by epoxidation and subsequenct reduction by metal hydrides, hydration, hydroboration or oxymercuration.

A hydroxyalkyl group A–B $CH_2CHOH$ or $CHOHCH_2$ may be dehydrated to give the group CH=CH by treatment with an acid anhydride such as acetic anhydride.

An amide group $CONHR^{11'}$ or $NHR^{11'}CO$ may be reduced to the amine using a reducing agent such as lithium aluminium hydride A ketone group may be converted to an amide CONH via the oxime by a Beckrnann rearrangement (Ogliaruso, M. A.; Wolfe, J. F., *ibid.* pp 450–451; Beckwith, A. L. J., *ibid.* pp 131 ff.)

A hydroxy group A or B may be converted to azido by activation and displacement e.g. under Mitsunobu conditions using hydrazoic acid or by treatment with diphenylphosphorylazide and base, and the azido group in turn may be reduced to arnino by hydrogenation.

A sulphur group A or B may be converted to the sulphoxide $S(O)_x$ by oxidation with peracids or a wide range of oxidants known to those skilled in the art (see Advanced Organic Chemistry (Ed. *March, J.*) (John Wiley and Sons, 1985), p 1089 and refs. cited therein).

Examples of groups $Z^{1'}, Z^{2'}, Z^{3'}, Z^{4'}, Z^{5'}$, are $CR^{1a'}$ where $R^{1a'}$ is a group convertible to $R^{1a}$, preferably methoxy.

$R^{1'}, R^{2'}, R^{3'}$ and $R^{4'}$ are preferably $R^1, R^2, R^3$ and $R^4$. $R^{1'}$ is preferably methoxy. $R^{2'}$ is preferably hydrogen. $R^{3'}$ is preferably $R^3$ such as hydrogen, carboxylate or vinyl. $R^4$ is preferably H or an N-protecting group such as as acyl or $(C_{1-6})$alkylsulphonyl.

Conversions of $R^{1a'}, R^{1'}, R^{2'}, R^{3'}$ and $R^{4'}$ and interconversions of $R^{1a}, R^1, R^2, R^3$ and $R^4$ are conventional. In compounds which contain an optionally substituted hydroxy group, suitable conventional hydroxy protecting groups which may be rcmoved without disrupting the remainder of the molecule include acyl and alkylsilyl groups.

For example $R^{1'}$ methoxy is convertible to $R^{1'}$ hydroxy by treaunent with lithium and diphenylphosphine (general method described in Ireland et. al. (1973) J.Amer.Chem.Soc.,7829) or HBr. Alkylation of the hydroxy group with a suitable alkyl derivative bearing a leaving group such as halide and a protected amino, piperidyl, amidino or guanidino group or group convertible thereto, yields, after conversion/deprotection, $R^1$ alkoxy substituted by optionally N-substituted amino, piperidyl, guanidino or amidino.

$R^3$ alkenyl is convertible to hydroxyalkyl by hydroboration using a suitable reagent such as 9-borabicyclo[3.3.1] nonane, epoxidation and reduction or oxymercuration.

$R^3$ 1,2-dihydroxy can be prepared from $R^{3'}$ alkenyl using osmium tetroxide or other reagents well known to those skilled in the art (see Advanced Organic Chemistry (Ed *Marchs J.*) (John Wiley and Sons, 1985), p 732–737 and refs. cited therein) or epoxidation followed by hydrolysis (see Advanced Organic Chemistry (Ed *March, J.*) (John Wiley and Sons, 1985), p 332,333 and refs. cited therein).

$R^3$ vinyl can be chain extended by standard homologation e.g by conversion to hydroxyethyl followed by oxidation to the aldehyde which is then subjected to a Wittig reaction.

Opening an epoxide $R^{3'}$ group with cyanide anion yields a $CH(OH)$—$CH_2CN$ group.

Opening an epoxide-containing $R^{3'}$ group with azide anion yields an azide derivative which can be reduced to the amine. Conversion of the amine to a carbamate is followed by ring closure with base to give the 2-oxooxazolidinyl containing $R^3$ group.

Substituents on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group, hydrolysis or oxidation as appropriate or reaction with an activated acid, isocyanate or alkoxyisocyanate. Primary and secondary hydroxy groups can be oxidised to an aldehyde or ketone respectively and alkyated with a suitable agent such as an organometallic reagent to give a secondary or tertiary alcohol as appropriate. A carboxylate group may be converted to an hydroxymethyl group by reduction of an ester of this acid with a suitable reducing agent such as lithium aluminium hydride.

Substituted 2-oxo-oxazolidinyl containing $R^3$ groups may be prepared from the corresponding aldehyde by conventional reaction with a glycine anion equivalent, followed by cyclisation of the resulting amino alcohol (M Grauert et al, Ann Chem (1985) 1817, Rozenberg et al, Angew Chem Int Ed Engl (1994) 33(1) 91). The resulting 2-oxo-oxazolidinyi group contains a carboxy group which can be converted to other $R^{10}$ groups by standard procedures.

Carboxy groups within $R^3$ may be prepared by Jones' oxidation of the corresponding alcohols $CH_2OH$ using chromium acid and sulphuric acid in waterlmethanol (E. R. H. Jones et al, J. C. S. 1946,39). Other oxidising agents may be used for this transformation such as sodium periodate catalysed by ruthenium trichloride (G. F. Tutwiler et al, J.Med Chem., 1987, 30(6), 1094), chromium trioxide-pyridine (G. Just et al, Synth. Commun. 1979. 9(7), 613), potassium permanganate (D. E. Reedich et al, J. Org. Chem.,1985,50 (19),3535, and pyridinium chlorochromate (D. Askin et al, Tetrahedron Letters, 1988, 29(3), 277.

The carboxy group may alternatively be formed in a two stage process, with an initial oxidation of the alcohol to the corresponding aldehyde using for instance dimethyl sulphoxide activated with oxalyl chloride (N.Cohen et al, J. Am. Chem. Soc., 1983, 105, 3661) or dicyclohexylcaodiimide (R. M. Wengler, Angew. Chim. Int. Ed. Eng., 1985, 24(2), 77), or oxidation with tetrapropylammonium perruthenate (Ley et al, J. Chem.Soc. Chem Commun,1987, 1625). The aldehyde may then be separately oxidised to the corresponding acid using oxidising agents such as silver (II) oxide (R.Grigg et al, J. Chem. Soc. Perkinl,1983, 1929), potassium permanganate (A.Zurcher, Helv. Chim. Acta., 1987, 70 (7), 1937), sodium periodate catalysed by ruthenium trichloride (T.Sakata et al, Bull. Chem. Soc. Jpn., 1988, 61(6),2025), pyridinium chlorochromate (R. S. Reddy et al, Synth. Commun., 1988, 18(51), 545) or chromium trioxide (R. M. Coates et al, J. Am. Chem. Soc.,1982, 104, 2198).

An $R^3$ $CO_2H$ group may also be prepared from oxidative cleavage of the corresponding diol, $CH(OH)CH_2OH$, using sodiun periodate catalysed by ruthenium trichloride with an acetontrile=arbontetrachloride-water solvent system (V. S. Martin et al, Tetrahedron Letters, 1988, 29(22), 2701).

$R^3$ groups containing a cyano or carboxy group may also be prepared by conversion of an alcohol to a suitable leaving group such as the corresponding tosylate by reaction with para-toluenesulphonyl chloride (M. R. Bell, J. Med. Chem., 1970, 13, 389), or the iodide using triphenylphosphine, iodine, and imidazole (G. Lange, Synth. Commun., 1990, 20, 1473). The second stage is the displacement of the leaving group with cyanide anion (L.A. Paquette et al, J. Org. Chem.,1979, 44 (25), 4603; P. A. Grieco et al, J. Org. Chem.,1988, 53 (16), 3658). Finally acidic hydrolysis of the nitrile group gives the desired acids (H.Rosemeyer et al, Heterocycles, 1985, 23 (10), 2669). The hydrolysis may also be carried out with base e.g. potassium hydroxide (H.Rapoport, J. Org. Chem.,1958, 23, 248) or enzymatically (T. Beard et al, Tetrahedron Asymmetry, 1993, 4 (6), 1085).

Other fimctional groups in $R^3$ may be obtained by conventional conversions of carboxy or cyano groups.

Tetrazoles are conveniently prepared by reaction of sodium azide with the cyano group (e.g. F. Thomas et al, Bioorg. Med. Chem. Lett., 1996, 6 (6), 631; K.Kubo et al, J. Med. Chem., 1993, 36,2182) or by reaction of azidotri-n-butyl stannane with the cyano group followed by acidic hydrolysis (P. L. Ornstein, J. Org. Chem., 1994, 59, 7682 and J. Med. Chem, 1996, 39 (11), 2219).

The 3-hydroxy-3-cyclobutene-1,2-dion-4-yl group (e.g. R. M. Soll, Bioorg. Med. Chem. Lett, 1993, 3 (4), 757 and W. A. Kinney, J. Med. Chem., 1992, 35 (25),4720) can be prepared by the following sequence:- (1) a compound where R3 is $(CH_2)_nCHO$ (n=0,1,2) is treated with tricthylamine, carbon tetrabromide triphenylphosphine to give initially $(CH_2)_nCH{=}CBr_2$; (2) dehydrobromination of this intermediate to give the corresponding bromoethyne derivative $(CH2)_nC{\equiv}CBr$ (for this 2 stage sequence see D. Grandjean et al, Tetrahedron Letters, 1994, 35 (21), 3529); (3) palladium-catalysed coupling of the bromoethyne with 4-(1-methylethoxy3-(tri-n-butylstannyl)cyclobut-3-ene-1,2-dione (Liebeskind et al, J. Org. Chem., 1990, 55, 5359); (4) reduction of the ethyne moity to —CH2CH2— under standard conditions of hydrogen and palladium on charcol catalysis(see Howard et al, Tetrahedron, 1980,36, 171); and finally (4) acidic hydrolysis of the methylethoxyester to generate the corresponding 3-hydroxy-3-cyclobutene-1,2-dione group R. M. Soll. Bioorg. Med. Chem. Lett, 1993, 3 (4), 757).

The tetrazol-5-ylaminocarbonyl group may be prepared from the corresponding carboxylic acid and 2-aminotetrazole by dehydration with standard peptide coupling agents such as 1,1'-carbonyldiimidazole (P. L. Ornstein et al, J. Med Chem, 1996, 39 (11), 2232).

The alkyl- and alkenyl-sulphonylcarboxarnides are similarly prepared from the corresponding carboxylic acid and the alkyl- or alkenyl-sulphonamide by dehydration with standard peptide coupling agents such as 1,1'-carbonyldiimidazole (P. L. Omstein et al, J.Med.Chem., 1996,39 (11), 2232).

The hydroxarnic acid groups are prepared from the corresponding acids by standard amide coupling reactions eg N. R. Patel et al, Tetrahedron, 1987, 43 (22), 5375.

2,4-thiazolidinedione groups may prepared from the aldehydes by condensation with 2,4-thiazolidinedione and subsequent removal of the olefinic double bond by hydrogenation.

The preparation of 5-oxo-1,2,4-oxadiazoles from nitriles is decribed by Y.Kohara et al, Bioorg. Med. Chem. Lett, 1995, 5(17), 1903.

1,2,4-triazol-5-yl groups may be prepared from the corresponding nitrile by reaction with an alcohol under acid conditions followed by reaction with hydrazine and then an $R^{10}$-substituted activated carboxylic acid (see JB Polya in 'Comprehensive Heterocyclic Chemistry' Edition 1 p762, Ed AR Katritzky and C W Rees, Pergamon Press, Oxford 1984 and J. J. Ares et al, J. Heterocyclic Chem., 1991, 28(5), 1197).

Other substituents on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsuiphonyl, alkenylsulphonyl or aminosulphonyl by conversion to a leaving group and substitution by the required group or oxidation as appropriate or reaction with an activated acid, isocyanate or alkoxyisocyanate. Primary and secondary hydroxy groups can be oxidised to an aldehyde or ketone respectively and alkyated with a suitable agent such as an organometallic reagent to give a secondary or tertiary alcohol as appropriate.

NH is converted to $NR^4$ by conventional means such as alkylation with an alkyl halide in the presence of base, acylation/reduction or reductive alkylation with an aldehyde.

Where one of $R^3$ and $R^6$, $R^7$, $R^8$ or $R^9$ contains a carboxy group and the other contains a hydroxy or amino group they may together form a cyclic ester or amide linkage. This linkage may form spontaneously during coupling of the compound of formula (IV) and the piperazine moiety or in the, presence of standard peptide coupling agents.

It will be appreciated that under certain circumstances interconversions may interfere, for example, hydroxy groups in A or B and the piperazine NH will require protection e.g. as a carboxy- or silyl-ester group for hydroxy and as an acyl derivative for piperidine nitrogen, during conversion of $R^{1a'}$, $R^{1'}$, $R^{2'}$, $R^{3'}$ or $R^{4'}$, or during the coupling of the compounds of formulae (IV) and (V) or (Vb).

Compounds of formulae (IV), (V) and (Vb) are known compounds, (see for example Smith et al, J. Amer. Chem. Soc., 1946, 68, 1301) or prepared analogously, see for example the references cited above for reaction variant (a).

An isocyanate of formula (IV) may be prepared conventionally. A 4-amino derivative such as 4-amino-quinoline, and phosgene, or phosgene equivalent (eg triphosgene) provide the isocyanate or it may be prepared more conveniently from a 4-carboxylic acid by a 'one-pot' Curtius Reaction with diphenyl phosphoryl azide (DPPA) [see T. Shiori et al. Chem. Pharm. Bull. 35, 2698–2704 (1987)].

The 4-carboxy derivatives are cormnercially available or may be prepared by 35 conventional procedures for preparation of carboxy heteroaromatics well known to those skilled in the art. For example, quinazolines may be prepared by standard routes as described by T. A. Williarnson in Heterocyclic Compounds, 6, 324 (1957) Ed. R. C. Elderfield. Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

The 4-amnino derivatives are conmnercially available or may be prepared by conventional procedures from a corresponding 4-chloro derivative by treatment with ammonia (O. G. Backeberg et. al., J. Chem Soc., 381, 1942.) or propylamine hydrochloride (R. Radinov et. al., Synthesis, 886, 1986).

A 4-chloroquinoline is prepared from the corresponding quinolin4-one by reaction with phosphorus oxychloride ($POCl_3$) or phosphorus pentachloride, $PCl_5$ A 4-chloroquinazoline is prepared from the corresponding quinazolin-4-one by reaction with phosphorus oxychloride ($POCl_3$) or phosphorus pentachloride, $PCl_5$. A quinazolinone and quinazolines may be prepared by standard routes as described by T. A. Williamson in Heterocyclic Compounds, 6, 324 (1957) Ed. R. C. Elderfield. Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

A 4-oxirane derivative is conveniently prepared from the 4-carboxylic acid by first conversion to the acid chloride with oxalyl chloride and then reaction with trimethylsilyldiazomethane to give the diazoketone derivative. Subsequent reaction with 5M hydrochloric acid gives the chloromethylketone. Reduction with sodium borohydride in aqueous methanol gives the chlorohydrin which undergoes ring closure to afford the epoxide on treatment with base, e.g. potassium hydroxide in ethanol-tetrahydrofuran.

If a chiral reducing agent such as (+) or (−)-B-chlorodiisopinocamphenylborane ['DIP-chloride'] is substituted for sodium borohydride, the prochiral chloromethylketone is converted into the chiral chlorohydrin with ee values generally 85–95% [see C. Bolm et al. Chem. Ber. 125, 1169–1190, (1992)]. Recrystallisation of the chiral epoxide gives material in the mother liquor with enhanced optical purity (typically ee 95%).

The (R)epoxide, when reacted with a piperazine derivative gives ethanolamine compounds as single diastereomers with (R)-stereochemistry at the benzylic position.

Alternatively, the epoxide may be prepared from the 4-carboxaldehyde by a Wittig approach using trimethylsulfonium iodide [see G A. Epling and K-Y Lin J. Het. Chem. 24, 853–857 (1987)], or by epoxidation of a 4-vinyl derivative.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5] naphthyridine-3-carboxylic acid, Joe T. Adams et al., J. Amer. Chem. Soc., 1946, 68, 1317). A 4-hydroxy-[1,5] naphthyridine can be converted to the 4-chloro derivative by heating in phosphorus oxychloride. A 4-amino 1,5-naphthyridine can be obtained from the 4-chloro derivative bv reaction with n-propylamine in pyridine. Similarly, 6methoxy-1,5-naphthyridine derivatives can be prepared from 3-amino-6-methoxypyridine.

1,5-Naphthyridines may be prepared by other methods well known to those skilled in the art (for examples see P.A. Lowe in "Comprehensive Heterocyclic Chemistry" Volume 2, p581–627, Ed A. R Katritzky and C. W. Rees, Pergarnon Press, Oxford, 1984).

The 4-hydroxy and 4-ainino-cirnolines may be prepared following methods well known to those skilled in the art [see A. R. Osborn and K. Schofield, J. Chem. Soc. 2100 (1955)]. For example. a 2-aminoacetopheneone is diazotised with sodium nitrite and acid to produce the 4-hydroxycinnoline with conversion to chloro and amino derivatives as described for 1,5-naphthyridines.

The substituted piperazines of formulae (V) and (Vb) are either commercially available or may be synthesised by hydrogenation of the corresponding pyrazines (eg von E. Felder et al. Helv. Chim. Acta 33, 888–896 (1960)], or by diborane reduction of a suitable lactam [eg H. L. Larkins et al. Tet. Lett. 27, 2721–2724 (1986)]. Chiral piperazines may be prepared from chiral 2-(S)- and 2-(R)-piperazinecarboxylic acid. Racemic piperazinc-2-carboxylic acid (cormnercially available) may be resolved by crystallisation of the (S)- and (R)-dicamphor-10-sulfonic acid salts [following the general method of K. Stingl et al. Tet Asymmetry 8, 979–982 (1997)described for preparation of 2-(S)-piperazinecarboxylic acid].

Piperazine-2-carboxylic acid may be differentially protected [following the procedure of C. F. Bigge et al. Tet. Lett. 30, 5193–5196 (1989)] by first reacting with 2-(t-butoxycarbonyloxyimino)2-phenylacetonitrile which selectively reacts on N-4, and then by reacting with benzylchloroformate which reacts on N-1. The 2-carboxylic acid is then methylated (conveniently with TMS-diazomethane). Hydrogenation (over Pd/C) then removes the carbobenzyloxy group, which may be alkylated with e.g. heptyl iodide or bromide in dimethylformamide with potassium carbonate as base. Reaction with trifluoroacetic acid (optionally in dichloromethane) removes the N4butoxycarbonyloxy group to afford the required 4-H piperazine.

The chiral piperazine-2-carboxylic acids may be elaborated to various derivatives, for example, an Arndt-Eistert procedure (involving silver salt mediated rearrangement of a diazoketone) will give chiral 2-acetic acid derivatives (initially via the methyl ester). Reduction of the intermediate ester with standard reducing agents such as lithium aluminium hydride will produce a hydroxymethyl derivative.

Compounds of formula (V) where n=1 or 2 may be prepared from the compound where n=0 by homologation eg starting from a compound of formula (V) where Y=$CO_2$H.

Conversions of $R^{1a'}$, $R^{1'}$, $R^{2'}$, $R^{3'}$ and $R^{4'}$ may be carried out on the intermediates of formulae (IV), (V) and (Vb) prior to their reaction to produce compounds of formula (I) in the same way as described above for conversions after their reaction.

The pharmaceutical compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable salt and/or N-oxide thereof is administered in the above-mentioned dosage range.

The compound of formula (I) may be the sole therapeutic agent in the compositions of the invention or a combination with other antibiotics or with a β-lactamase inhibitor may be employed.

Compounds of formula (I) are active against a wide range of organisms including both Gram-negative and Gram-positive organisms.

The following examples illustrate the preparation of certain compounds of formula (I) and the activity of certain compounds of formula (X) against various bacterial organisms.

EXAMPLE 1

[2S]-1-Heptyl-4-[2-(R,S)-hydroxy-2-(6-methoxyquinolin-4-yl)ethyl]-2-hydroxymethylpiperazine (a) [2S]-Piperazine-2-carboxylic acid di-(S)-camphor-10-sulfonic acid salt This was prepared from [2R,S]-piperazine-2-carboxylic acid dihydrochloride by the method of K. Stingl et al. [*Tetrahedron: Asymmetry*, 8, 979–982 (1997)] and had >99% enantiomeric excess (ee) by chiral HPLC.

(b)[2S]-1-Benzyloxycarbonyl-4-t-butoxycarbonyl-2-methoxycarbonylpiperazine

A solution of [2S]-1-benzyloxycarbonyl-4-t-butoxycarbonylpiperazine-2-carboxylic acid [prepared from Example 1(a) by the method of Bigge et al. *Tet. Letters* 30, 5193 (1989)] (16 g) in methanol (5 ml) and acetonitrile (50 ml) was treated with diisopropylethylamine (5.7 ml) and a 2M solution of trimethylsilyldiazomethane in hexane (26.3 ml) and stirred overnight at room temperature. The reaction mixture was evaporated and chromatographed on silica gel eluting with 0–10% ethyl acetate-hexane to afford the title compound as a colourless oil (9.0 g). MS (+ve ion electrospray) m/z 379 (MH+).

(c) [2S]-4-t-Butoxycarbonyl-2-methoxycarbonylpiperazine

A solution of Example 1(b)(4.39g) in methanol (50ml) was hydrogenated over 10% palladium on carbon (0.50 g) until uptake of hydrogen ceased. It was filtered and evaporated to afford the title compound as a colourless oil. MS (+ve ion electrospray) m/z 245 (MH+)

(d) [2S]- 4-t-Butoxycarbonyl-2-hydroxymethylpiperazine

A solution of Example 1(c) in dry tetrahydrofuran (40ml) at 0° C. was treated with lithium aluminium hydride (0.50 g) and the mixture was stirred at 0° C. for 1.5 hours. The cooled solution was treated dropwise with a solution of 2M sodium hydroxide until a white precipitate had formed. Dichloromethane and anhydrous sodium sulfate were added and the solution was filtered and evaporated to give a pale yellow oil (3.0 g). MS (+ve ion electrospray) m/z 217 (MH+).

(e) [2S]- 4-t-Butoxycarbonyl-1-heptyl-2-hydroxymethylpiperazine

A solution of Example 1(d) (25 ml) was treated with anhydrous potassium carbonate (1.76 g) and n-heptyl iodide (2.88 g) and stirred at room temperature for 18 hours. The mixture was evaporated to dryness, treated with sodium carbonate solution, extracted with dichloromethane, dried, and chromatographed on silica gel eluting with 30–50% ethyl acetate-hexane to afford a pale yellow oil (1.5 g) with ee>98% by chiral HPLC [Chirapak AD column; with hexane-ethanol (97:3)]. MS (+ve ion electrospray) m/z 315 (MH+).

(f) [R,S]-2-(6Methoxyquinolin-4-yl)oxirane

A solution of 6-methoxyquinoline-4-carboxylic acid (10 g) in dichloromethane was heated under reflux with oxalyl chloride (5 ml) and dimethylformnamide (2 drops) for 1 hour and evaporated to dryness. The residue, in dichloromethane (100 ml) was treated with a 2M solution of trimethylsilyldiazomethahe in hexane (50 ml) and stirred at room temperature for 18 hours. 5M Hydrochloric acid. (150 ml) was added and the solution was stirred at room temperature for 3 hours. It was basified with sodium carbonate solution, extracted with ethyl acetate and chromatographed on silica gel eluting with ethyl acetate-hexane to give the chloromethyl ketone (4.2 g). This was reduced by treatment with sodium borohydride (0.27 g) in methanol (40 ml) and water (2 ml). The product was extracted with dichloromethane and evaporated to dryness. It was treated with potassium hydroxide (2.9 g) in ethanol (10 ml) and tetrahydrofuran (100 ml). The reaction mixture was diluted with ethyl acetate, washed with water, dried and evaporated. The product was chromatographed on silica gel eluting with ethyl acetate to give the title compound as a solid (2.3 g). MS (+ve ion electrospray) m/z 202 (MH+)

(g) Title compound

A solution of Example 1 (e) (0.53 g) in dichloromethane (20m1) and trifluoroacetic acid was stirred at 0° C. for 30 minutes and allowed to warm to room temperature over 2 hours. It was evaporated to dryness and azeotroped with toluene to afford [2S]-1-heptyl-2-hydroxymethylpiperazine trifluoroacetate salt as a foam. The salt was dissolved in acetonitrile (3 ml), and treated with diusopropylethylamine (0.544 g) until pH 6. Example 1(f) (0.509 g) and lithium perchlorate (0.179 g) were added and the mixture was stirred at room temperature for 48 hours. [method of J. E. Chateauneuf et al. *J. Org. Chem.* 56, 5939–5942]. The reaction rriixture was evaporated and basified with sodium carbonate solution and extracted (x3) with dichloromethane. The organic fraction was dried and chromatographed on silica gel eluting with 50–100% ethyl acetate-hexane to afford the title compound as an oil (0.248 g).
MS (+ve ion electrospray) m/z 416 (MH+).

EXAMPLE 2

[2R]-1-Heptyl-4-[2-(R,S)-hydroxy-2-(6-methoxyquinolin-4-yl)ethyl]-2-hydroxymethylpiperazine (a) [2R]-Piperazine-2-carboxylic acid di-(R) camphor-10sulfonic acid salt.

This was prepared from [2R,S]-piperazine-2-carboxylic acid dihydrochloride by the method of K. Stingl et al. [*Tetrahedron: Asymmetry*, 8, 979–982 (1997)] using (R)-camphor-10-sulfonic acid and had ee >99% by chiral HPLC [Nucleosil Chiral-1 column]

(b) Title compound

[2R]-Piperazine-2-carboxylic acid di-(R)camphor-10-sulfonic acid salt was converted to [2R]-4-t-butoxycarbonyl-1-heptyl-2-hydroxymethylpiperazine by the method of Example 1 (be). Deprotection of a sample (0.38 g ) with trifluoroacetic acid in dichloromethane, followed by reaction with Example 1 (f)(0.36 g) by the method of Example 1 (g) gave an oil (0.275 g).
MS (+ve ion electrospray) m/z 416 (MH+).

Example 3

[2S]-1-Hepty-4-[2(R)-hydroxy-2-(6-methoxyquinolin-4-yl)ethyl]-2-hydroxymethylpiperazine dioxalate (a) [R]-2-(6-Methoxyquinolin-4-yl)oxirane This was prepared from 6-methoxyquinoline-4-carboxylic acid by the method of Example 1(f) except that the chloromethylketone (20 g) was reduced with (+)-B-chlorodiisopinocamphenylborane (40 g) in dichloromethane (400 ml) at room temperature for 18 hours followed by treatment with diethanolamine (30 g) for 3 hours. The product was chromatographed on silica gel eluting with ethyl acetate-hexane to give the chloroalcohol (16.8 g), which was dissolved in tetrahydrofuiran (100 ml) and reacted with sodium hydroxide (2.6 g) in water (13 ml) for 1.5 hours. The reaction mixture was evaporated to dryness and chromatographed on silica gel eluting with ethyl acetate-hexane to give the title compound as a solid (10.4 g) (84% ee by chiral HPLC). Recrystallisation from ether-pentane gave mother-liquor (7.0 g) (90% ec). MS-(+ve ion electrospray) m/z 202 (MH+)

The absolute stereochemistry was defined to be (R) by an NMR study on the Mosher's esters derived from the product obtained by reaction with 1-t-butylpiperazine (see Example 18).

(b) Title Compound

Reaction of Example 3(a) (0.1 g) and [S]-1-heptyl-2-hydroxymethylpiperazine (0.106 g), by the method of Example 1 (g). gave the title compound (0.1 g), as an oil with 90% ee.
MS (+ve ion electrospray) m/z 416 (MH+)

The oil was treated with 2 molar equivalents of oxalic acid in ether and the resulting solid was collected, trirurated with ether, to afford the dioxalate salt as a white solid.

Example 4

[2S]-1-Heptyl-4-[2-(S)-hydroxy-2-(6-methoxyquinolin-4y1)ethyl]-2-hydroxymethylpiperazine dioxalate The pair of diastereomers of Example I were separated by preparative HPLC (Chiralcel OD, eluting with ethanol-hexane 1:9). Collection of the faster eluting isomer (retention time 9.4 min) and treatment with 2 molar equivalents of oxalic acid in ether afford the title compound as a white solid. The slower eluting isomer (retention time 11.2 min) furnished compound of Example 3 (free base).

EXAMPLE 5

[2R]-1-Heptyl-4-[2S)-hydroxy-2-(6-methoxyquinolin-4-yl)ethyl]-2-hydroxymethylpiperazine dioxalate The pair of diastereomers of Example 2 were separated by preparative HPLC (Chiralcel O D, eluting with ethanol-hexane 1:9). Collection of the faster eluting isomer (retention time 7.3 min) and treatment with 2 molar equivalents of oxalic acid in ether afforded the title compound as a white solid.

EXAMPLE 6

[2R]-1-Heptyl-4-[2(R)-hydroxy-2-(6-methoxyquinolin-4-yl)ethyl]-2-hydroxymethylpiperazine dioxalate The pair of diastereomers of Example 2 were separated by preparative HPLC (Chiralcel OD, eluting with ethanol-hexane 1:9). Collection of the slower eluting isomer (retention time 15.4 min)and treatment with 2 molar equivalents of oxalic acid in ether afforded the title compound as a white solid.

EXAMPLE 7

[2R,S]-1-Heptyl-2-hydroxyethyl-4-[2-(R,S)-hydroxy-2-(6-methoxyquinolin-4-yl)ethyl]piperazine (a) [2R,S]-2-Ethoxycarbonylmethyl-1-heptyl-3-oxo-piperazine A solution of [2R,S]-2-ethoxycarbonylmethyl-3-oxo-piperazine (10 g) in dry dimethylforarnmide (20 ml) was treated with anhydrous potassium carbonate (7.5 g) and n-heptyl iodide (12.2 g) and stirred at room temperature for 18 hours. The mixture was evaporated and basified with sodium carbonate solution, extracted (x3) with dichloromethane, washed with brine, dried over sodium sulfate and evaporated to dryness. The product (12 g) was chromatographed on silica gel eluting with 10–50% ethyl acetate-hexane to afford an oil (12 g).
MS (+ve ion electrospray) m/z 285 (MH+).

(b) [2R,S]-1-Heptyl-2-hydroxyethylpiperazine

A solution of Example 7(a) in dry tetrahydrofuran (35 ml) at 0° C. was treated with lithium aluminium hydride (1.0 g) and the mixture was heated under reflux for 18 hours. The cooled solution was treated dropwise with a solution of 2N sodium hydroxide until a white precipitate had formed. Dichloromethane and anhydrous sodium sulfate were added and the solution was filtered and evaporated to give an oil (I .98 g).
MS (+ve ion electrospray) m/z 229 (MH+).

(c) Title compound

A solution of Example 7(b) (0.17 g) in acctonitrile (2 ml) was treated with Example 1 (f) (0.15 g) and lithium perchlorate (80 mg) and the mixture was stirred at room temperature for 24 hours. It was evaporated and basified with sodium carbonate solution and extracted (x3) with chloroform. The organic fraction was dried and chromatographed on silica gel eluting with ethyl acetate-hexane (1:1) followed by methanol-ethyl acetate (5:95) to afford the title compound as an oil (0.13.8 g).
MS (+ve ion electrospray) m/z 430(MH+).

EXAMPLE 8

[2R,S]-2-Carboxymethyl-1-beptyl-4-[2-(R,S) hydroxy-2-(6-methoxyquinolin-4-yl)ethyl]piperazine trihydrochloride (a) [2R,S]-2-Ethoxycarbonylmethyl-1-heptylpiperazine A solution of Example 7(a) (1.3 g) in dry tetrahydrofuran (10 ml) was treated with a 10M solution of borane-methyl sufide complex in tetrahydrofiran (1.65 ml) and the solution was stirred at room temperature for 18 hours. The solution was stirred with an excess of ethanolic-hydrogen chloride at room temperature for 30 minutes, evaporated to dryness., basified with sodium carbonate solution and extracted with dichloromethane. The product was chromatographed on silica gel eluting with 2–20% ethanol-dichloromethane to afford an oil (0.11 g).
MS (+ve ion electrospray) m/z 271 (MH+).

(b) [2R,S]-2-Ethoxycarbonylmethyl-1-heptyl-4-[2-(R,S)-hydroxy-2-(6-methoxyquinolin-4-yl)ethyl]piperazine.

Prepared from Example 8(a) (0.195 g) and Example 1(f) by the method of Example 7(c), with a reaction time of 72 hours, to afford an oil (0.19 g).
MS (+ve ion electrospray) m/z 472 (MH+).

(c) Title Compound

A solution of Example 8(b) (0.10 g) in 2M hydrochloric acid (15 ml) was heated under reflux for 6 hours and evaporated to afford a foam (0.105 g).
MS (+ve ion electrospray) m/z 444 (MH+).

EXAMPLE 9

[2S]-2-Carboxymethyl-1-heptyl+[2-(R,S)hydroxy-2-(6-methoxyquinolin-4-yl)ethyl]piperazine trihydrochloride (a) [2S]-1-Benzyloxycarbonyl-4-t-butoxycarbonyl-2-methoxycarbonylmethylpiperazine A solution of of [2R]-1-benzyloxycarbonyl4-t-butoxycarbonylpiperazine-2-carboxylic acid (prepared as in Example 1(b) and 2(a)) (4.7 g) in ethyl acetate (70 ml) containing N-methylmorpholine (1.76 ml) at 0° C. was treated with isobutyl chloroformate (2.37 ml) for 3 hours and the solution was filtered and added to an excess of diazomethane and left at room temperature for 18 hours. It was evaporated to dryness to afford the diazoketone, which was dissolved in dry methanol (120 ml) and treated with silver benzoate (1.99 g) in triethylamine (19.9 ml), with cooling in ice. The solution was stirred in the dark at room temperature for 18 hours, evaporated to dryness, dissolved in ethyl acetate, washed with sodium bicarbonate solution and dried over sodium sulfate. It was chromatographed on silica gel, eluting with ethyl acetate-hexane to afford an oil (3.1 5 g) (94% ee by chiral HPLC).

(b) [2S]-4-t-Butoxycarbonyl-1-heptyl-2-methoxycarbonylmethylpiperazine

Example 9(a) was hydrogenated over 10% palladium-carbon in methanol and the product reacted with n-heptyl iodide by the method of Example l(e) to afford an oil.
MS (+ve ion electrospray) m/z 357 (MH+).

(c) [2S]-1-Heptyl-2-methoxycarbonylmethylpiperaine

Example 9(b) (1.05 g) was reacted with trifluoroacetic acid (30 ml) in dichloromethane (30 ml) at room temperature for 2.5 hours and evaporated to dryness. Basification with sodium carbonate and extraction with dichloromethane gave the free base as an oil (0.79 g).

(d) [2S]-2-Methoxycarbonylmethyl-1-heptyl-4-[2-(R,S)-hydroxy-2-(6-methoxyquinolin-4-yl)ethyl]piperazine This was prepared from Example 9(c) (0.75 g) and Example l(f) (0.88 g) by the method of Example 7(c) to afford an oil (0.89 g).
MS (+ve ion electrospray) m/z 458 (MH+).
(e) Title compound
A solution of Example 9(d) (0.6 g) was heated in 5M hydrochloric acid (200 ml) for 10 hours and evaporated to dryness to afford a foam (0.8 g).
MS (+ve ion electrospray) m/z 444 (MH+).

EXAMPLE 10

[2R]-2-Carboxymethyl-1-heptyl-4-[2R,S)-hydroxy-2-(6-methoxyquinolin-4-yl)ethyl]piperazine trihydrochloride This was prepared from [2S]-1-benzyloxycarbonyl-4-t-butoxycarbonyl-piperazine-2-carboxylic acid (Example 1(b))by the method of Example 9.
MS (+ve ion electrospray) m/z 444 (NH+).

EXAMPLE 11

[3R]-3-Carboxymethyl-1-heptyl-4-[2-(R)-hydroxy-2-(6-methoxyquinolin-4-yl)ethyl]piperazine tris (trifluoroacetate)
(a) [3R]-1-t-Butoxycarbonyl-3-carboxymethyl)4-[2-(R)hydroxy-2-(6-methoxyquinolin-4-yl)ethyl]piperazine
This was prepared from [3R]- I-t-butoxycarbonyl-3-methoxycarbonylmethylpiperazine (prepared in Example 9(b)) (1.0 g) and Example 3(a) (0.857 g) by the method of Example 1(g), as a foam (0.37 g).
MS (+ve ion electrospray) m/z 460 (MH+).
(b) Title Compound
Example 11(a) (0.35 g) was treated with trifluoroacetic acid in dichloromethane and then reacted with n-heptyl iodide by the Method of Example 1(e), followed by silica gel chromatography in ethyl acetate, to afford an oil (0.25 g). This was further purified by reverse phase HPLC eluting with acetonitrile-water –0.1% trifluoroacetic acid, and concentrated to give a foam.
MS (+ve ion electrospray) m/z 444 (MH+).

EXAMPLE 12

[3S]-1-Heptyl-3-[2-hydroxyetbyl]-4-[2-(R,S) hydroxy-2-(6-methoxyquinolin-4-yl)ethyl]piperazine dioxalate
(a) [3S]-Heptyl-3-methoxycarbonylmethyl-4-[2-(R,S)-hydroxy-2-(6-methoxyquinolin-4-yl)ethyl]piperazine
Prepared from Example 24(c) (0.325 g) and Example 1(f) (0.275 g) in acetonitrile (3 ml) containing lithium perchlorate (0.096 mg) at 50° C. by the method of Example 1(g), to give an oil (0.22 g).
MS (+ve ion electrospray) m/z 458 (MH+).
(b) Title Compound
A solution of Example 12(a) (26mg) in dry tetrahydrofuiran (5 ml) at 0° C. was treated with lithium aluminium hydride (6 mg) and the mixture was stirred for 35 minutes. 2M Sodium hydroxide was added and the solution filtered, evaporated to dryness and the product chromatographed on silica gel in ethyl acetate followed by 10% methanol-dichloromethane to afford an oil (13 mg). Treatment with 2 molar equivalents of oxalic acid in ether afforded the title compound as a white solid.
MS (+ve ion electrospray) m/z 430 (MH+)

EXAMPLE 13

[2S]-1-Heptyl-4-[2(R,S)-hydroxy-2-(6-metboxyquinolin-4yl)ethyll-2-hydroxyaminocarbonylmethylpiperazine A solution of Example 9 (0.10 g) in anhydrous DMF (2 ml) was treated with 1-(3-dimethylaminopropyl)-3-ethylcarbodiimide hydrochloride (69mg), 1 -hydroxy-7-azaberizotriazole (49 mg) and N-methylmorpholine (0. 14 ml). After stirring at room temperature for 45 minutes, hydroxylamine hydrochloride (50 mg) was added and stirring continued overnight. Solvent was then removed in vacuo and the residue was chromatographed on silica gel eluting with 10% methanol/ dichloromethane, then again on preparative silica TLC plates eluted with 1% ammonia/9% methanol/ dichloromethane to give the title compound (30 mg, 36%).
MS (+ve ion electrospray) m/z 459 (MH+).

EXAMPLE 14

[2R]-1 -Heptyl-2-cyanomethyl-4-[2-(R)-hydroxy-2-(6-methoxyquinolin-4-yl)ethyl]piperazine dioxalate
(a) [2S]-4-t-Butoxycarbonyl-1-heptyl-2-chloromethylpiperazine
A solution of Example l(e) (0.32 g) in dichloromethane (5 ml) and diisopropylethylamine 0.158 g) was treated with tosyl chloride (0.213 g) at room temperature for 2 days. The reaction mixture was evaporated to dryness, sodium carbonate solution was added and it was extracted with dichloromethane, dried over sodium sulfate and evaporated to dryness to afford an oil (0.33 g).
MS (+ve ion electrospray) m/z 333, 335 (MH+).
(b) [2R]-1-Heptyl-2-cyanomethyl piperazine
Example 14(a) (0.33 g) in dry DMF (3 ml) was treated with sodium cyanide (0.145 g) and potassium iodide (I crystal) at room temperature for 3 days. The mixture was poured into dilute sodium carbonate solution and extracted with dichloromethane, washed with water, dried over sodium sulfate and evaporated to dryness. The resulting oil was chromatographed on silica gel eluting with ethyl acetate-hexane to afford an oil (0.19 g). This was treated with trifluoroacetic acid (3 ml) in dichloromethane (3 ml) for 3 hours and evaporated. It was basified with sodium carbonate, extracted with dichloromethane, dried over sodium sulfate and evaporated to give an oil (0.12 g).
MS (+vc ion electrospray) m/z 224 (MH+).
(c) Title Compound
Example 14(b) (0.12 g) was reacted with Example 3(a) (0.162 g; 86% ee) and lithium perchlorate (0.057 g) by the method of Example 1 (g) to afford an oil (0.10 g). Treatment with 2 molar equivalents of oxalic acid in ether afforded the title compound as a white solid.
MS (+ve ion electrospray) m/z 425 (MH+)

EXAMPLE 15

[2R]-1-Heptyl-2-[2-aminoethyl]-[2-(R)hydroxy-2-6-methoxyquinolin-4-yl)ethyl]piperazine dioxalate A solution of Example 14 free base in dry ether(10 ml) at room temperature was treated with a IM solution of lithium aluminium hydride in tetrahydrofilran (0.45 ml) and the mixture was stirred overnight. Tetrahydrofuran (5 ml) was added followed by 2M sodium hydroxide and sodium sulfate, and the mixture filtered and evaporated to dryness to give an oil. This was chromatographed on silica gel, eluting with ethyl acetate, then 1% ammonia in methanol-dichloromethane (1:9) to afford an oil (0.04 g). Treatment with 2 molar equivalents of oxalic acid in ether afforded the title compound as a white solid.
MS (+ve ion electrospray) m/z 429 (MH+)

EXAMPLE 16

1-Hepty]-4-[3-(6-methoxyquinolin-4-yl) propylpiperazine]

(a) 1-Heptylpiperazine t-Butyl-1-piperazinecarboxylate (1.86 g) in dimethylformamide (15 ml) was stirred with 1-iodoheptane (1.8 ml) and potassium carbonate (1.5 g) for 2 hours. The mixture was diluted with water, extracted with ethyl acetate, dried and evaporated to afford an oil (2.6 g). The product was treated with trifluoroacetic acid (5 ml) in dichloromethane (10 ml) for 2 hours, evaporated and triturated with ether to afford a white solid (1.17 g).

(b) 1-Heptyl-4-[3-(6methoxyquinolin-4-yl)propanoylpiperazine.

A solution of 6-methoxyquinoline-4-propanoic acid [prepared by the method of J.Walker, *J Chem.Soc.*, (1947), 1684] (0.2 g) in DMF (5 ml) was treated with 1-(3-dimethylaminopropyl)-3-ethylcarbodiimide hydrochloride (0.19 g), Example 16(a) (0.17 g) and N,N-diisopropylethylamnine (0.34 ml). The mixture was stirred at room temperature overnight, then poured into water and extracted with ether. Ethereal extracts were washed with water and brine, dried and evaporated. The crude product was chromatographed on silica gel (10 g) eluted with 5% methanol/dichloromethane to give the title compound (0.14 g, 40%).

MS (+ve ion electrospray) m/z 398 (MH+).

(c) Title Compound.

To a solution of Example 16(b) (0.10 g) in anhydrous THF (5 ml) was added lithium aluminium hydride (40 mg). The mixture was stirred at room temperature for 6 6 hours, then treated dropwise with 8% aqueous sodium hydroxide until a white precipitate formed. Anhydrous sodium sulphate was added and the mixture was filtered through Celite. The filtrate was evaporated and the residue was chromatographed on silica gel (4 g) eluting with 5% methanol/dichloromethane to give the title compound (0.07 g, 72%).

MS (+ve ion electrospray) m/z 384 (MH+).

EXAMPLE 17

1-Heptyl-4-[2-(R,S)-hydroxy-2-(6-methoxyquinolin-4-yl)ethyl]piperazine

A solution of Example 16(a) (92 mg) in tetrahydrofiran (3 ml) was reacted with 1.6M butyl lithium in hexane (0.31 ml) at O° C. for 10 minutes and allowed to warm up to room temperature when Example 1 (f) (0.1 g) was added and the solution was heated at 80° C. for 18 hours. The mixture was diluted with water, extracted with ethyl acetate, and chromatographed on silica gel eluting with methanol-chlorofonn-ammonia (5:95:0.5) to give a brown oil (47 mg).

MS (+ve ion electrospray) m/z 386 (MH+).

EXAMPLE 18

1-Heptyl-4-[2-(R)-hydroxy-2-(6-methoxyquinolin-4-yl)ethyl]piperazine oxalate

Example 3(a) (0.3 g) was dissolved in acetonitrile (3 ml) and treated with lithium perchlorate (0.33 g) and Example 16(a) (0.5 g). The mixture was stirred for 3 days then evaporated and purified on silica gel eluting with methanol-ethyl acetate (5:95) to give a golden oil (0.48 g). with 92% ee (by chiral HPLC).

MS (+ve ion electrospray) m/z 386 (MH+).

The absolute stereochemistry of Example 18 was defined by reacting the product with both (S)-(+)-and (R)-(–)-α-methoxy-α-(trifluoromethyl)phenylacetyl chloride in dichloromethane containing dirnethylaminopyridine to afford the corresponding (S )-(+)-and (R)-(–)-Mosher ester derivatives. Comparison of Δδ values of these derivatives by NMR [Ohtani et al. *J Am. Chem. Soc.* 113, 4092–4096 (1991)], allowed (R)-stereochemistry to be assigned at C-2. Thus, the oxirane from which this compound was derived (Example 3(a)) also has the (R) configuration.

EXAMPLE 19

1-Heptyl4-[2-(S)-hydroxy-2-(6-methoxyquinoin-4-yl)ethyl]piperazine oxalate (a) [S]-2-(6-methoxyquinolin-4yl)oxirane This was prepared by the method of Example 3(a) except that the chloromethylketone was reduced with (-)-B-chlorodiisopinocamphenylborane. The product had 90% ee.

MS (+ve ion electrospray) m/z 202 (MH+).

(b) 4-[2-(S)-Hydroxy-2-(6-methoxyquinolin-4-yl)ethyl] piperazine

Example 19(a) (0.15 g) was dissolved in acetonitrile (3 ml) and treated with lithium perchlorate (0.08 g) and 1-t-butyloxycarbonylpiperazine (0.25 g). The mixture was stirred for 24h then evaporated and purified on silica gel eluting with ethyl acetate to give a yellow gum (0.26 g) The gum was dissolved in dichloromethane (5 ml) and treated with trifluoroacetic acid for 3 hours then evaporated. The residue was treated with methanol, chloroform and solid potassium carbonate. Filtration and evaporation afforded an oil (0.2 g).

MS (+ve ion electrospray) m/z 288 (MH+).

(c) Title Compound

Example 19(b) (0.2 g) was dissolved in N,N-dimethylfomiarnide and treated with heptyl iodide (0.13 ml) and potassium carbonate (0.13 g). After 2 hours the mixture was diluted with ethyl acetate, washed with water and brine then evaporated. The crude product was purified on silica gel eluting with methanol-ethyl acetate (5:95–10:90) then methanol-chloroform-ammonia (0:90.1) to give the title compound as a gum (0.21 g).

MS (+ve ion electrospray) m/z 386 (MH+).

EXAMPLE 20

1-Octyl-4-[2-(R)-hydroxy-2-(6-methoxyquinolin-4-yl)ethyl]piperazine oxalate (a) 1-[2(R)-hydroxy-2-(6-methoxyquinolin-4-yl)ethyl] piperazine This was prepared from 1-t-butoxycarbonylpiperazine and Example 1(f) by the method of Example 1(g).

(b) Title compound

A mixture of Example 20(a) (0.1 g), potassium carbonate (0.16 g), potassium iodide (60 mg) and I-bromooctane (0.07 ml) in DMF (2 ml) was stirred overnight at room temperature. The mixture was filtered and evaporated. The residue was dissolved in ethyl acetate and the solution was washed with water, dried and evaporated. The crude product was chromatographed on silica gel (5 g) eluting with 0–2% methanol/ethyl acetate. Eluted product was converted into the oxalate salt by treatment with 0.1M oxalic acid in ether to give the title compound (58 mg).

MS (+ve ion electrospray) m/z 400 (MH+).

EXAMPLE 21

1-Hexyl-4-[2-(R)-hydroxy-2-(6-methoxyquinolin-4yl)ethyl]piperazine oxalatel

This compound was prepared from Example 1(f) (0.10 g), by the method of Example 20, using 1-iodohexane (0.08 ml)

as the alkylating agent (potassium iodide omitted). Yield of oxalate salt 37 mg.
MS (+ve ion electrospray) m/z 372 (MH+).

EXAMPLE 22

1-(5-Methyl-1-hexyl)-4-[2-(R)-hydroxy-2-(6-methoxyquinolin-4-yl)ethyl]piperazine oxalate This compound was prepared from Example 1 (f) (0.10 g) by the method of Example 20, using 1-bromo-5-methylhexane (0.064 ml) as the alkylating agent. Yield of oxalate salt 42 mg.
MS (+ve ion electrospray) m/z 386 (MH+).

EXAMPLE 23

1-Heptyl-4-[N-(6-methoxyquinolin-4-yl)formamidol piperazine

6-Methoxyquinoline-4-carboxylic acid (1 g. 4.9 mmol) in 1,2-dichloromethane (15 ml) was treated with triethylamine (0.7 ml, 5.0 mmol) and stirred for 15 minutes. Diphenylphosphorylazide (1.1 ml, 5.1 mmol) was added and the mixture was stirred at room temperature for 1.5 hours and then heated under reflux for 30 minutes. A mixture of Example 16(a) (0.115 g, 6.3 mmol) and triethylamine (1.5 ml, 10.7 mmol) in 1,2-dichloroethane (5 ml) was added and the mixture was stirred overnight. It was diluted with dichloromethane, washed with sodium carbonate solution, water and brine. dried and evaporated. Purification on silica gel eluting with 10% methanol-ethyl acetate gave a yellow solid (0.30 g, 16%).
MS (+ve ion electrospray) m/z 385 (MH+).

EXAMPLE 24

[9aS, 3S]-3-(6-metboxyquinolin-4-yl)-8-heptylhcxahydro-pyrazino [2,1-c][1,4]oxazin-3(4H)-one (a) [2S]-1-Benzyloxycarbonyl-2-methoxycarbonylpiperazine Example 1(b) (3.6 g, 9.5 mmol) was dissolved in trifluoroacetic acid (50 ml). After 2h the solution was evaporated to dryness. The residue was partitioned between ethyl acetate and saturated aqueous sodium bicarbonatc solution. The ethyl acetate extract was dried and evaporated giving the title compound as a yellow oil(2.6 g,100%).
MS (+ve ion electrospray) m/z 279 (MH+).
(b) [2S]-1-Benzyloxycarbonyl4-heptyl-2-methoxycarbonylpiperazine Example 24(a) (2.6 g, 9.5 mmol) was N-heptylated according to the procedure for Example 1(e), giving the title compound as an oil (2.9 g, 81%).
MS (+ve ion electrospray) m/z 377 (MH+).
(c) [2S]-4-heptyl-2-methoxycarbonylpiperazine Example 2(b) (2.9 g, 7.7 mmol) was dissolved in ethanol (120 ml) and hydrogenated over 10% palladium on charcoal (1 g). Filtration and evaporation afforded the title compound as a yellow oil, (1.5 g, 81%).
MS (+ve ion electrospray) m/z 243 (MH+).
(d) Title Compound A mixture of Example 1(f) (1.4 g, 6.6 mmol), lithium perchlorate (0.75 g, 7.1 mmol) and Example 24(c) (1.5 g, 6.5 mmol) in acetonitrile (1 2 ml) was heated to 70° C. for 4 hours. The mixture was allowed to cool then partitioned between ethyl acetate—dilute aqueous sodium chloride solution. The organic extract was dried and evaporated. Repeated chromatography on silica (elute with firstly a gradient of methanol in dichloromethane, then secondly with a gradient of ethyl acetate in hexane)afforded the title compound as an oil (140 mg, 6%).
MS (+ve ion electrospray)m/z 412 (MH$^+$).

EXAMPLE 25

[9aS,3R]-3-(6-methoxyquinolin-yl)-8-heptylhexahydro pyrazino[2,1-c][1,4]oxazin-3(4H)-one The title compound (50 mg) was prepared in 2% yield by chromatographic separation from the isomeric analogue, Example 24.
MS (+ve ion electrospray)m/z 412 (MH$^+$)

EXAMPLE 26

[9aR,3R]-(6-methoxy quinolin-4-yl)-8-heptylhexahydro-pyrazinol-2,1- c][1,4]oxazine-3 (4H)-one This was prepared by the same route and in similar overall yield as Example 24, except starting from [2R]-1-benzyloxycarbonyl-4-t-butoxycarbonyl-2-methoxycarbonylpiperazine (Example 2(b))
MS (+ve ion electrospray)m/z 412 (MH$^+$).

EXAMPLE 27

[9aR,3S]-3-(6methoxy quinolin-4-yl)-8-heptylhexahydropyrazinol-2,1-c][1,4]oxazine-3(4H)-one This was prepared by the same route and in similar overall yield as Example 25, except starting from [2R]-1-benzyloxycarbonyl-2-methoxycarbonylpiperazine by chromatographic separation from Example 26.
MS (+ve ion electrospray) M/z 412 (MH$^+$)

EXAMPLE 28

[3R]-1-Heptyl-3-[2-hydroxyethyl]-4-[2-(R,S)-hydroxy-2-(6-methoxyquinolin-4-yl)ethyl]piperazine oxalate (a) [3R]- 1 -Heptyl-3-methoxycarbonylmethyl-4-[2-(R,S)-hydroxy-2-(6-methoxyquinolin-4-yl)ethyl]piperazine Prepared by reacting [3 R]-1-heptyl-3-methoxycarbonylmethylpiperazine (itself prepared from [2R]-1-benzyloxycarbonyl-4-t-butoxycarbonyl-2-methoxycarbonylpiperazine (Example 2(b)) by the method of Examples 24(a)c)) with Example 1(f) by the same method as for Example 12, to give an oil (0.40 g).
MS (+ve ion electrospray) m/z 458 (MH+).
(b) Title compound Prepared from Example 28(a) by reduction with lithium aluminium hydride according to the method of Example 12, followed by treatment with one equivalent of oxalic acid in ether affording the title compound as a white solid. MS (+ve ion electrospray) m/z 430 (MH+)

EXAMPLE 29

[3R]-1-Heptyl-3-hydroxymethyl-4-[2-(R)-hydroxy-2-(6-methoxyquinolin-4-yl)ethyl]piperazine This was prepared from Example 26 (0.22 g) by reduction with lithium aluminium hydride (2 equivalents) in tetrahydrofuran (10 ml) at 0° for 0.Sh followed by workup with 40% aqueous sodium hydroxide and ethyl acetate.Chromatography on silica elutin with a gradient of 0–5% methanol in dichloromethane gave the title product as an oil (0.12 g, 56%) which was dissolved in chloroform and converted to the oxalate salt by the addition of 1 equivalent of oxalic acid in ether.
MS (+ve ion electrospray) m/z 415 (MH+).

EXAMPLE 30

[3S]-1-Heptyl-3-hydroxymethyl-4-[2-(S)-hydroxy-2-(6-methoxyquinolin-4-yl)ethyl]piperazine This was prepared from Example 24 according to the method of Example 29. Yield of free base 20 mg, 17%. This was converted to the oxalate salt.
MS (+ve ion electrospray) m/z 415 (MH+).

EXAMPLE 31

[3S]-1-Heptyl-3-hydroxymethyl-4-[2-(R)-hydroxy-2-(6-methoxyquinolin-4-yl)ethyl]piperazine This was prepared from Example 25 according to the method of Example 29. Yield of free base 11 mg, 28%. This was converted to the oxalate salt.
MS (+ve ion electrospray) m/z 415 (MH+).

EXAMPLE 32

[3R]-1-Heptyl-3hydroxymethyl-4-[2-(S)-hydroxy-2-6-methoxyquinolin-4-yl)ethyl]piperazine This was prepared from Example 27 according to the method of Example 29. Yield of free base 6 mg, 30%. This was converted to the oxalate salt.
MS (+ve ion electrospray) m/z 415 (MH+).

EXAMPLE 33

1-(3-phenoxypropyl)-4-[2-(R)-hydroxy-2-(6-methoxyquinolin-4-yl)ethyl]piperazine
(a) 4-[(R)-2-Hydroxy-2-(6-methoxyquinolin-4-yl)-ethyl]-piperazine-1-carboxylic acid tert-butyl ester
(R)-2-(6-Methoxyquinolin-4-yl)oxirane (Example 3a) (4.30 g, 21.37 mmol) was dissolved in acetonitrile (30 mL). To the solution was added piperazine-1-carboxylic acid tert-butyl ester (7.17 g, 38.47 mmol) and lithium perchlorate (2.27 g, 106.4 mmol). The resulting slurry was stirred at room temperature for 10 hours and then concentrated in vacuo. The residue was partitioned between ethyl acetate and water and the organic phase dried over magnesium sulfate. Concentration in vacuo afforded a colourless oil which was subjected to purification by column chromatography on silica gel using a dichloromethane/methanol gradient. This provided the desired compound as a colourless oil (7.65 g, 92%).
MS (APCI+) m/z 388 (MH+).
(b) [24-(R)-hydroxy-2-(6-methoxyquinolin-4-yl)ethyl] piperazine
Example 33(a) (3.50 g) was dissolved in dichloromethane (10 mL) and trifluoroacetic acid (10 mL) was added. The resulting solution was stirred at room temperature for 5 hours and then concentrated in vacuo. The residue was stirred with methanol, chloroform and solid potassium carbonate for 1h, then filtered and evaporated, affording the product as an oil (2.1 g).
MS (APCI+) m/z 288 (MH+).
(c) 3-Phenoxypropionaldehyde
3-Phenoxypropan-1-ol (3.17 g, 20.86 mmol) was dissolved dichloromethane (25 mL) and pyridinium chlorochromate (6.76 g, 31.28 mmol) was added. The slurry was stirred at room temperature for 1 hour and then filtered through silica gel eluting with an ethyl acetate/hexanes gradient. The desired compound was isolated as a yellow oil (1.1 g).
MS (APCI+) m/z 149 (M+-1).
(d) Title compound
Example 33(b) (170 mg, 0.59 mmol) was dissolved in dichloromethane (3mL) and methanol (1 mL) and Example 33(c) (223 mg, 1.49 mmol) was added. The solution was stirred at room temperature over 3A molecular seives and sodium cyanoborohydride (112 mg, 1.78 mmol) was added. Stirring was then continued for 10 hours. The volatiles were removed in vacuo and the residue partitioned between ethyl acetate and water. The organic phase was dried over magnesium sulfate and then concentrated in vacuo. The residue was subjected to purification by column chromatography on silica gel eluting with a methanol/dichloromethane gradient. This provided the desired compound as a yellow oil (91 mg, 36%).
MS (APCI+) m/z 422 (MH+).
A solution of the oil (91 mg) in dichloromethane (1 mL) was added to oxalic acid (39 mg) in diethyl ether (10 mL) to generate the dioxalate salt. The title compound was isolated by centrifugation, washing with diethyl ether and subsequent drying in vacuo.

EXAMPLE 34

1-f3-(3,4-Dimethoxyphenyl)propyl]4-[2(R,S) hydroxy-2-(6-methoxyquinolin-4-yl)ethyl]piperazine A solution of 3-(3,4-dimethoxyphenyl)-propanol (1.0 g) in dichloromethane was treated with triethylamine (0.6 g) and methanesulphonyl chloride (0.6 g). Affer 3h the solution was washed with water, dried, and evaporated. The residue was dissolved in DMF (10 ml) and treated with [2-(R,S)-hydroxy-2-(6-methoxyquinolin-4-yl)ethyl]piperazine (1.1 g) (prepared from Example 1(f) by an analogous procedure to Example 33(b)) and potassium carbonate (0.66 g). The mixture was heated at 80° C. for 3h, then evaporated to dryness. The residue was partitioned between ethyl acetate and saturated aqueous sodium bicarbonate solution. The organic extract was dried and evaporated and the residue chromatographed on silica eluting with a methanol-dichloromethane gradient, affording the title compound as an oil (0.46,). This was converted to a dioxalate salt in the usual way.
MS (+ve ion electrospray) m/z 466(MH+).

EXAMPLE 35

1-[3-(1,3-Dihydro-2-oxobenzimidazol-1-yl)-propyl] 4-[2-(R)-hydroxy-2-(6-methoxyquinolin-4-yl)ethyl] piperazine Example 33(b) was dissolved in N.N'-dimethylformamide (3mL). To the solution was added potassium carbonate (125 mg, 0.91 mmol), tetra n-butylammonium iodide (67 mg, 0.18 mmol) and 1-(3-chloropropyl)-1.3-dihydrobenzoimidazol-2-one (205 mg, 0.807 mmol). Stirring at 60° C. was continued for 10 hours and then the mixture was concentrated in vacuo. The residue was purified by column chromatography on silica gel to provide the desired product as a colourless oil (48 mg, 17%).
MS (APCI+) m/z 462 (MH+).
A solution of the oil (48 mg) in dichloromethane (1 mL) was added to oxalic acid (19 mg) in diethyl ether (10 mL) to generate the dioxalate salt. The title compound was isolated by centrifugation, washing with diethyl ether and subsequent drying in vacuo.

The following compounds were prepared by procedures analogous to those described herein:

Formula (I), $Z_1$-$Z_5$=CH

| Example | $R^1$ | A | B | n | $R^3$ | $R^4$ |
|---|---|---|---|---|---|---|
| 36 (S,R, R,S) | 6-MeO | CH(OH) | $CH_2$ | 0 | 3-COOH | $(CH_2)_6CH_3$ |
| 37 (R,R, S,S) | 6-MeO | CH(OH) | $CH_2$ | 0 | 3-COOH | $(CH_2)_6CH_3$ |
| 38 | 6-MeO | CH(OH) | $CH_2$ | 0 | 2-COOH | $(CH_2)_6CH_3$ |
| 39 | 6-MeO | NH | $CH_2$ | 1 | H | $(CH_2)_6CH_3$ |
| 40 | 6-MeO | CH(OH) | $CH_2$ | 0 | 2-$CH_2CO_2Et$ | $(CH_2)_6CH_3$ |
| 41 | 6-MeO | NH | CO | 1 | H | $(CH_2)_6CH_3$ |
| 42 | 6-MeO | CH(OH) | $CH_2$ | 0 | 2-$CO_2CH_3$ | $(CH_2)_6CH_3$ |
| 43 | 6-MeO | CH(OH) | $CH_2$ | 0 | H | $(CH_2)_6OH$ |
| 44 | 6-MeO | CH(OH) | $CH_2$ | 0 | H | $(CH_2)_5CN$ |
| 45 | 6-MeO | CH(OH) | $CH_2$ | 0 | H | $(CH_2)_6CN$ |

Biological Activity

The MIC (µg/ml) of test compounds against various organisms was determined: S. aureus Oxford, S. aureus WCUH29, S. aureus Carter 37, E. faecalis I, M. catarrhalis Ravasio, S. pneumoniae R6.

Examples 1–10, 12, 17–22 and 28–32 have an MIC of less than or equal to 1 µg/ml against one or more of the above range of gram positive and gram negative bacteria.

Examples 11, 13–16, 23–27, 33, and 3640 showed an MIC of less than or equal to 16 µg/ml against one or more of the above range of gram positive and gram negative bacteria.

What is claimed is:

1. A compound of formula (I) or a pharmaceutically acceptable salt and/or N-oxide thereof:

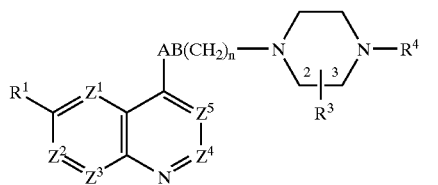

wherein:
one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;

$R^1$ is selected from hydroxy; $(C_{1-6})$ alkoxy optionally substituted by $(C_{1-6})$alkoxy, amino, piperidyl, guanidino or amidino optionally N-substituted by one or two $(C_{1-6})$alkyl, acyl or $(C_{1-6})$alkylsulphonyl groups, $NH_2CO$, hydroxy, thiol, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$ alkoxy-substituted $(C_{1-6})$alkyl; halogen; $(C_{1-6})$alkyl; $(C_{1-6})$alkylthio; nitro; azido; acyl; acyloxy, acylthiol; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups, or when one of $Z^1$, $Z^2$, $Z^3$, $Z^4$ and $Z^5$ is N, $R^1$ may instead be hydrogen;

$R^{1a}$ is selected from H and the groups listed above for $R^1$;
$R^3$ is hydrogen; or
$R^3$ is in the 2- or 3-position and is: carboxy; $(C_{1-6})$ allkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy $(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $R^3$ is in the 2- or 3-position and is $(C_{1-4})$alkyl or ethenyl optionally substituted with any of the groups listed above for $R^3$ and/or 0 to 3, groups $R^{12}$ independently selected from:

thiol; halogen; $(C_{1-6})$alkylthio; trifluoromethyl; azido; $(C_{1-6})$alkoxycarbonyl; $(C_{1-6})$alkylcarbonyl; $(C_{2-6})$ alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$ alkylcarbonyl, $(C_{2-6})$alkenyloxycarbonyl, $(C_{2-6})$ alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$ alkenylcarbonyl; amino optionally mono- or disubstituted by $(C_{1-6})$alkoxycarbonyl, $(C_{1-6})$ alkylcarbonyl, $(C_{2-6})$alkenyloxycarbonyl, $(C_{2-6})$ alkenylcarbonyl, $(C_{1-6})$alkyl, $(C_{2-6})$alkenyl, $(C_{1-6})$ alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$ alkoxycarbonyl, $(C_{1-6})$alkylcarbonyl, $(C_{2-6})$ alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$alkylsulphonyl; $(C_{2-6})$ alkenylsulphonyl; or $(C_{1-6})$aminosulphonyl wherein the amino group is optionally substituted by $(C_{1-6})$ alkyl or $(C_{2-6})$alkenyl; provided that when $R^3$ is disubstituted with hydroxy or amino and carboxy containing substituents these may optionally together form a cyclic ester or amide linkage, respectively; wherein $R^{10}$ is selected from $(C_{1-4})$alkyl; $(C_{2-4})$alkenyl; aryl; a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{4-6})$alkenylsulphonyl, $(C_{1-6})$alkoxycarbonyl, $(C_{1-6})$alkylcarbonyl, $(C_{2-6})$ alkenyloxycarbonyl or $(C_{2-6})$alkenylcarbonyl and optionally further substituted by $(C_{1-6})$alkyl or $(C_{2-6})$alkenyl; cyano; or tetrazolyl;

$R^4$ is a group —$CH_2$—$R^5$ in which $R^5$ is selected from: $(C_{3-12})$alkyl; hydroxy$(C_{3-12})$alkyl; $(C_{1-12})$alkoxy$(C_{3-12})$alkyl; $(C_{1-12})$alkanoyloxy$(C_{3-12})$alkyl; $(C_{3-6})$ cycloalkyl$(C_{3-12})$alkyl; hydroxy-, $(C_{1-12})$alkoxy- or $(C_{1-12})$alkanoyloxy-$(C_{3-6})$cycloalkyl$(C_{3-12})$alkyl; cyano$(C_{3-12})$alkyl; $(C_{2-12})$alkenyl; $(C_{2-12})$alkynyl; tetrahydrofuryl; mono- or di-$(C_{1-12})$alkylamino$(C_{3-12})$alkyl; acylamino$(C_{3-12})$alkyl; $(C_{1-12})$alkyl- or acyl-aminocarbonyl$(C_{3-12})$alkyl; mono- or di-$(C_{1-12})$ alkylamino(hydroxy)$(C_{3-12})$alkyl; optionally substituted phenyl($C_{1-2}$)alkyl, phenoxy($C_{1-2}$)alkyl or phenyl(hydroxy)($C_{1-2}$)alkyl; optionally substituted diphenyl($C_{1-2}$)alkyl; optionally substituted phenyl ($C_{2-3}$)alkenyl; optionally substituted benzoyl or benzoyl($C_{1-3}$)alkyl; optionally substituted heteroaryl or heteroaryi($C_{1-2}$)alkyl; and optionally substituted heteroaroyl or heteroaroylmethyl;

n is 0, 1 or 2;

AB is $NR^{11}CO$, $CO-CR^8R^9$ or $CR^6R^7-CR^8R^9$ or when n is 1 or 2, AB may instead be $O-CR^8R^9$ or $NR^{11}-CR^8R^9$, or when n is 2 AB may instead be $CR^6R^7-NR^{11}$ or $CR^6R^7-O$, provided that when n is 0, B is not CH(OH), and wherein:

each of $R^6$ and $R^7$, $R^8$ and $R^9$ is independently selected from: H; thiol; ($C_{1-6}$)alkylthio; halo; trifluoromethyl; azido; ($C_{1-6}$)alkyl; ($C_{2-6}$)alkenyl; ($C_{1-6}$)alkoxycarbonyl; ($C_{1-6}$)alkylcarbonyl; ($C_{2-6}$)alkenyloxycarbonyl; ($C_{2-6}$)alkenylcarbonyl; hydroxy, amino or aminocarbonyl optionally substituted as for corresponding substituents in $R^3$; ($C_{1-6}$)alkylsulphonyl; ($C_{2-6}$)alkenylsulphonyl; or ($C_{1-6}$)aminosulphonyl wherein the amino group is optionally substituted by ($C_{1-6}$)alkyl or ($C_{1-6}$)alkenyl; or $R^6$ and $R^8$ together represent a bond and $R^7$ and $R^9$ are as above defined; and each $R^{11}$ is independently H, trifluoromethyl, ($C_{1-6}$)alkyl, ($C_{2-6}$)alkenyl, ($C_{1-6}$)alkoxycarbonyl, ($C_{1-6}$)alkylcarbonyl, aminocarbonyl wherein the amino group is optionally substituted by ($C_{1-6}$)alkoxycarbonyl, ($C_{1-6}$)alkylcarbonyl, ($C_{2-6}$)alkenyloxycarbonyl, ($C_{2-6}$)alkenylcarbonyl, ($C_{1-6}$)alkyl or ($C_{2-6}$)alkenyl and optionally further substituted by ($C_{1-6}$)alkyl or ($C_{2-6}$)alkenyl;

or wherein one of $R^3$ and $R^6$, $R^7$, $R^8$ or $R^9$ contains a carboxy group and the other contains a hydroxy or amino group they may together form a cyclic ester or amide linkage wherein:

'heterocyclic' is an aromatic and non-aromatic, single and fused, ring containing up to four hetero-atoms in each rine selected from oxygen, nitrogen and sulphur, and having from 4 to 7 rin atoms, which rings may be unsubstituted or substituted by up to three groups selected from amino, halogen, ($C_{1-6}$)alkyl, ($_{1-6}$)alkoxy, halo($C_{1-6}$)alkyl, hydroxy, carboxy, carboxy salts, ($C_{1-6}$)alkoxycarbonyl, ($C_{1-6}$)alkoxycarbonyl($C_{1-6}$)alkyl, aryl, and oxo groups, and wherein any amino group forming part of a single or fused non-aromatic heterocyclic ring as defined above is optionally substituted by ($C_{1-6}$)alkyl optionally substituted by hydroxy, ($C_{1-6}$)alkoxy, thiol, ($C_{1-6}$)alykthio, halo or trifluoromethyl, acyl or ($C_{1-6}$)alkylsulphonyl groups;

'aryl' is phenyl or naphthyl, optionally substituted with up to five groups selected from halogen, mercapto, ($C_{1-6}$)alkyl, phenyl, ($C_{1-6}$)alkoxy, hydroxy($C_{1-6}$)alkyl, mercapto ($C_{1-6}$)alkyl, halo($C_{1-6}$)alkyl, hydroxy, amino, nitro, cyano, carboxy, ($C_{1-6}$)alkylcarbonyloxy, ($C_{1-6}$)alkoxycarbonyl, formyl and ($C_{1-6}$)alkylcarbonyl groups;

'acyl' is ($C_{1-6}$)alkoxycarbonyl, formyl or ($C_{1-6}$)alkylcarbonyl.

2. A compound according to claim 1 wherein one of $Z^1$, $Z^2$, $Z^3$, $Z^4$ and $Z^5$ is N and one of $Z^3$ and $Z^5$ if not N is $CR^{1a}$ and the remainder are CH, or one of $Z^1$, $Z^2$, $Z^3$, $Z^4$ and $Z^5$ is $CR^{1a}$ and the remainder are CH.

3. A compound according to claim 2 wherein $Z^5$ is CH or N, $Z^3$ is CH or CF and $Z^1$, $Z^2$ and $Z^4$ are each CH, or $Z^1$ is N, $Z^3$ is CH or CF and $Z^2$, $Z^4$ and $Z^5$ are each CH.

4. A compound according to claim 1 wherein R is methoxy, amino($C_{3-5}$)alkyloxy, guanidino($C_{3-5}$)alkyloxy, piperidyl($C_{3-5}$)alkyloxy, nitro or fluoro.

5. A compound according to claim 1 wherein $R^3$ is hydrogen, ($C_{1-4}$) alkyl, ethenyl or optionally substituted 1-hydroxy-($C_{1-4}$) alkyl; or $R^3$ contains carboxy, optionally substituted aminocarbonyl, cyano or 2-oxo-oxazolidinyl optionally substituted by $R^{10}$; and wherein $R^3$ is in the 3-position.

6. A compound according to claim 1 wherein n is 0 and either A is CHOH and B is $CH_2$ or A is NH and B is CO.

7. A compound according to claim 1 wherein $R^4$ is ($C_{5-10}$)alkyl, unsubstituted phenyl($C_{2-3}$)alkyl or unsubstituted phenyl($C_{3-4}$)alkenyl.

8. A compound according to claim 1 selected from:

[2S]-1-Heptyl-4-[2-(R,S)-hydroxy-2-(6-methoxyquinolin-4-yl)ethyl]-2-hydroxymethylpiperazinel;[2R]-1-Heptyl-4-[2-(R,S)-hydroxy-2-(6-methoxyquinolin-4-yl)ethyl]-2-hydroxymethylpiperazinel;

[2S]-1-Heptyl-4-[2-(R)-hydroxy-2-(6-methoxyquinolin-4-yl)ethyl]-2-hydroxymethylpiperazine dioxalatel;

[2S]-1-Heptyl-4-[2-(S)-hydroxy-2-(6-methoxyquinolin-4-yl)ethyl]-2-hydroxymethylpiperazine dioxalate;

[2R]-1-Heptyl-4-[2-(S)-hydroxy-2-(6-methoxyquinolin-4-yl)ethyl]-2-hydroxymethylpiperazine dioxalatel

[2R]-1-Heptyl-4-[2-(R)-hydroxy-2-(6-methoxyquinolin-4-yl)ethyl]-2-hydroxymethylpiperazine dioxalate;

[2R,S]- 1-Heptyl-2-hydroxyethyl-4-[2-(R,S)-hydroxy-2-(6-methoxyquinolin-4-yl)ethyl]piperazinel;

[2R,S]-2-Carboxymethyl-1-heptyl-4-[2-(R,S)-hydroxy-2-(6-methoxyquinolin-4-yl)ethyl]piperazine trihydrochloridel;

[2S]-2-Carboxymethyl-1-heptyl-4-[2-(R,S)-hydroxy-2-(6-methoxyquinolin-4-yl)ethyl]piperazine trihydrochloride;

[2R]-2-Carboxymethyl-1-heptyl-4-[2-(R,S)-hydroxy-2-(6-methoxyquinolin-4-yl)ethyl]piperazine trihydrochloride;

[3R]-3-Carboxymethyl-1-heptyl-4-[2-(R)-hydroxy-2-(6-methoxyquinolin-4-yl)ethyl]piperazine tris (trifluoroacetate);

[3S]-1-Heptyl-3-[2-hydroxyethyl]4-[2-(R,S)-hydroxy-2-(6-methoxyquinolin-4-yl)ethyl]piperazine dioxalate;

[2S]-1-Heptyl-4-[2-(R,S)-hydroxy-2-(6-methoxyquinolin-4-yl)ethyl]-2-hydroxyaminocarbonylmethylpiperazine;

[2R]-1-Heptyl-2-cyanomethyl-4-[2-(R)-hydroxy-2-(6-methoxyquinolin-4-yl)ethyl]piperazine dioxalate;

[2R]-1-Heptyl-2-[2-aminoethyl]-4-[2-(R)-hydroxy-2-(6-methoxyquinolin-4-yl)ethyl]piperazine dioxalate;

1-Heptyl-4-[6-(6-metboxyquinolin-4-yl)propyl] piperazine;

1-Heptyl-4-[2-(R,S)-hydroxy-2-(6-methoxyquinolin-4-yl)etlhy]piperazine;

1-Heptyl-4-[2-(R)-hydroxy-2-(6-methoxyquinolin-4-yl) ethyl]piperazine oxalate;

1-Heptyl-4-[2-(S)-hydroxy-2-(6-methoxyquinolin-4-yl) ethyl]piperazine oxalate;

1-Octyl-4-[2-(R)-hydroxy-2-(6-methoxyquinolin-4-yl) ethyl]piperazine oxalate;

1-Hexyl-4-[2-(R)-hydroxy-2-(6-methoxyquinolin-4-yl) ethyl]piperazine oxalate; 1-(5-Methyl-1-hexyl)-4-[2-(R)-hydroxy-2-(6-methoxyquinolin-4-yl)ethyl] piperazine oxalate;

1-Heptyl-4-[N-(6methoxyquinolin-4-yl)formamido]
  piperazine;
[9aS, 3S]-3-(6-methoxyquinolin-4-yl)-8-
  heptylhexahydropyrazino [2,1-c][1,4]oxazin-3(4H)-
  one;
[9aS,3R]-3-(6-methoxyquinolin-4-yl)-8-
  heptylhexahydropyrazino[2,1-c][1,4]oxazin-3 (4H)-
  one;
[9aR,3R]-(6-methoxy quinolin-4-yl)-8-
  heptylhexahydropyrazino[2,1-c][1,4]oxazine-3 (4H)-
  one;
[9aR,3S]-3-(6-methoxy quinolin-4-yl)-8-
  heptylhexahydropyrazino[2,1-c][1,4]oxazine-3 (4H)-
  one;
[3R]-Heptyl-3-[2-hydroxyethyl]4-[2-(R,S)-hydroxy-2-
  (6-methoxyquinolin-4-yl)ethyl]piperazine oxalate;
[3R]-1-Heptyl-3-hydroxymethyl-4-[2-(R)-hydroxy-2-(6-
  methoxyquinolin-4-yl)ethyl]piperazine,
[3S]-1-Heptyl-3-hydroxymethyl-4-[2-(S)-hydroxy-2-(6-
  methoxyquinolin-4-yl)ethyl]piperazine;
[3S]-1-Heptyl-3-hydroxymethyl-4-[2-(R)hydroxy-2-(6-
  methoxyquinolin-4-yl)ethyl]piperazine;
[3R]-1-Heptyl-3-hydroxymethyl-4-[2-(S)-hydroxy-2-(6-
  methoxyquinolin-4-yl)ethyl]piperazine;
1-(3-phenoxypropyl)-4-[2-(R)-hydroxy-2-
  (6methoxyquinolin-4-yl)ethyl]piperazine;
1-[3-(3,4-Dimethoxyphenyl)-propyl]-4-[2-(R,S)-
  hydroxy-2-(6-methoxyquinolin-4-yl)ethyl]piperazine;
  and 9. A pharmaceutical composition comprising a compound of formula (I) or a pharmaceutically acceptable salt/and or N-oxide thereof according to claim 1, and a pharmaceutically acceptable carrier.

10. A method of treatment of bacterial infections in mammals, particularly in man, which method comprises the administration to a mammal in need of such treatment of an effective amount of a compound of formula (I) or a pharmaceutically acceptable salt/and or N-oxide thereof according to claim 1.

11. A process for preparing compounds of formula (I), or a pharmaceutically acceptable salt and/or N-oxide thereof according to claim 1, which process comprises: (a) reacting a compound of formula (IV) with a compound of formula (V):

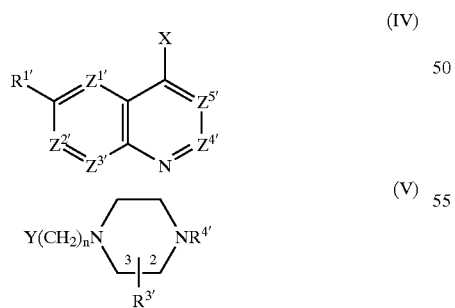

wherein $Z^1$, $Z^2$, $Z^3$, $Z^4$ and $Z^5$, m, n, $R^1$, $R^3$ and $R^4$ are as defined in formula (I), and X and Y may be the following combinations:

(i) X is M and Y is $CH_2CO_2R^x$, $CH_2CHO$ or $CH_2COW$
(ii) X is $CO_2R^y$ and Y is $CH_2CO_2R^x$
(iii) one of X and Y is $CH=SPh_2$ and the other is CHO
(iv) X is $CH_3$ and Y is CHO
(v) X is $CH_3$ and Y is $CO_2R^x$
(vi) X is $CH_2CO_2R^y$ and Y is $CO_2R^x$
(vii) X is $CH=PR^z_3$ and Y is CHO
(viii) X is CHO and Y is $CH=PR^z_3$
(ix) X is halogen and Y is $CH=CH_2$
(x) one of X and Y is COW and the other is $NHR^{11'}$
(xi) one of X and Y is $(CH_2)_p$-W and the other is $(CH_2)_q NHR^{11'}$ or $(CH_2)_q OH$
(xii) one of X and Y is CHO and the other is $NHR^{11'}$, or where n=0
(xiii) X is A–B-$(CH_2)_n$-W or A–B-$(CH_2)_{n-1}$-CHO and Y is H
(xiv) X is NCO and Y is H
(xv) X is $CH_3$ and Y is H
(xvi) X is $COCH_2W$ and Y is H
(xvii) X is $CH=CH_2$ and Y is H
(xviii) X is oxirane and Y is H in which W is a leaving group, $R^x$ and $R^y$ are $(C_{1-6})$alkyl and $R^z$ is aryl or $(C_{1-6})$alkyl; or (b) reacting a compound of formula (IV) with a compound of formula (Vb):

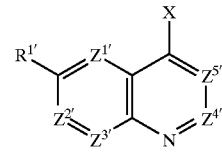

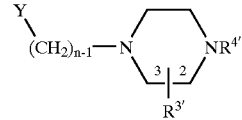

wherein $Z^1$, $Z^2$, $Z^3$, $Z^4$ and $Z^5$, m, n, $R^1$, $R^3$ and $R^4$ are as defined in formula (I), X is $CH_2NH/R^{11'}$ and Y is CHO or COW;

in which $Z^{1'}$, $Z^{2'}$, $Z^{3'}$, $Z^{4'}$, $Z^5$, $R^{11'}$, $R^{1'}$, $R^{3'}$, and $R^{4'}$ are $Z^1$, $Z^2$, $Z^3$, $Z^4$, $Z^5$, $Z^{11}$, $R^1$, $R^3$ and $R^4$ or groups convertible thereto, and thereafter optionally or as necessary converting $Z^{1'}$, $Z^{2'}$, $Z^{3'}$, $Z^{4'}$, $Z^5$, $R^{11'}$, $R^{1'}$, $R^{3'}$ and $R^{4'}$ to $Z^1$, $Z^2$, $Z^3$, $Z^4$, $Z^5$, $R^{11'}$, $R^1$, $R^3$ and $R^4$, converting A-B to other A-B, interconverting $Z^1$, $Z^2$, $Z^3$, $Z^4$, $Z^5$, $R^{11}$, $R^1$, $R^3$ and/or $R^4$ and forming a pharmaceutically acceptable salt/and or N-oxide thereof.

* * * * *